(12) United States Patent
Noda et al.

(10) Patent No.: US 8,029,744 B2
(45) Date of Patent: Oct. 4, 2011

(54) METHOD OF LIQUID DROPLET FORMATION AND TRANSPORT APPARATUS THEREFOR AND PARTICLE MANIPULATING APPARATUS

(75) Inventors: Hideyuki Noda, Kokubunji (JP); Yoshinobu Kohara, Yokohama (JP); Kenko Uchida, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 526 days.

(21) Appl. No.: 12/084,990

(22) PCT Filed: Mar. 7, 2006

(86) PCT No.: PCT/JP2006/304382
§ 371 (c)(1),
(2), (4) Date: May 14, 2008

(87) PCT Pub. No.: WO2007/057989
PCT Pub. Date: May 24, 2007

(65) Prior Publication Data
US 2009/0020555 A1    Jan. 22, 2009

(30) Foreign Application Priority Data
Nov. 16, 2005  (JP) .................................. 2005-331865

(51) Int. Cl.
*B01L 3/00* (2006.01)
*G01N 11/00* (2006.01)
*G01N 21/00* (2006.01)
*G01N 13/00* (2006.01)

(52) U.S. Cl. .......... 422/504; 422/81; 422/501; 422/521; 422/523; 435/287.2; 435/6; 73/64.52; 73/53.01; 222/53

(58) Field of Classification Search .................. None
See application file for complete search history.

(56) References Cited

U.S. PATENT DOCUMENTS
6,023,540 A    2/2000  Walt et al.
(Continued)

FOREIGN PATENT DOCUMENTS
JP        11-243997         3/1998
(Continued)

OTHER PUBLICATIONS
International Search Report of PCT/JP2006/304382 mailed Jun. 13, 2006.
(Continued)

*Primary Examiner* — In Suk Bullock
*Assistant Examiner* — Jennifer Wecker
(74) *Attorney, Agent, or Firm* — Stites & Harbison PLLC; Juan Carlos A. Marquez, Esq.

(57) ABSTRACT

The present invention provides an apparatus for efficiently transporting or dispensing transport objects including not only particles but also liquid samples. A liquid in a first liquid transport pipe (3) is fed at a liquid feed velocity (V1), and a liquid droplet is formed toward an open end of a second liquid transport pipe (4) disposed with an air gap (11) in between. The particle is released into the liquid droplet, so that the particle is enclosed in the liquid droplet. Suction with a liquid feed velocity (V2) is applied to the inside of the second liquid transport pipe. Since the relationship between V1 and V2 is V1<V2, the liquid droplet, after reaching the open end (10) of the second liquid transport pipe, is sheared off by suction, thereby forming a liquid section in the second liquid transport pipe. Thus, the particle in the liquid section, held under surface tension on a gas-liquid phase boundary, can be transported into a particle array container with stability in conjunction with the liquid section.

20 Claims, 25 Drawing Sheets

U.S. PATENT DOCUMENTS

| | | | | |
|---|---|---|---|---|
| 6,555,389 | B1 * | 4/2003 | Ullman et al. | 436/514 |
| 2004/0265181 | A1 * | 12/2004 | Noda et al. | 422/99 |
| 2006/0257994 | A1 * | 11/2006 | Noda et al. | 435/287.2 |

FOREIGN PATENT DOCUMENTS

| | | |
|---|---|---|
| JP | 2000-346842 | 4/2000 |
| JP | 2002-544494 | 5/2000 |
| JP | 2003-315336 | 4/2002 |
| JP | 2004-333401 | 5/2003 |
| JP | 2005-017224 | 6/2003 |
| JP | 2005-027559 | 7/2003 |
| WO | WO 00/67907 | 5/2000 |

OTHER PUBLICATIONS

Hideyuki Noda et al., "Single Bead Capturing Technique by Capillary Vacuum Tweezers", Extended Abstracts (the 51$^{st}$ Spring Meeting, 2004, The Japan Society of Applied Physics and Related Societies, No. 3, cover sheet and p. 1436, and 3 pages of English translation.

Stephen P.A. Fodor et al., "Light-Directed, Spatially Addressable Parallel Chemical Synthesis", Feb. 15, 1991, Science, vol. 251, pp. 767-773.

Mark Schena et al., "Quantitative Monitoring of Gene Expression Patterns With a Complementary DNA Microarray", Science, vol. 270, Oct. 20, 1995, pp. 467-470.

Tadashi Okamoto et al., "Microarray Fabrication with Covalent Attachment of DNA Using Bubble Jet Technology", Nature Biotechnology, vol. 18, Apr. 2000, pp. 438-441.

R. Jerrold Fulton et al., "Advanced Multiplexed Analysis with the FlowMetrix™ System", Clinical Chemistry 43:9, 1997, pp. 1749-1756.

Yoshinobu Kohara et al., "DNA Probes on Beads Arrayed in a Capillary, 'Bead-array', Exhibited High Hybridization Performance", Nucleic Acids Research (2002)1 vol. 30, No. 16, 7 pages.

Hideyuki Noda et al., "Automated Bead Alignment Apparatus Using a Single Bead Capturing Technique for Fabrication of a Miniaturized Bead-Based DNA Probe Array", Analytical Chemistry, vol. 75, No. 13, Jul. 1, 2003, pp. 3250-3255.

* cited by examiner

METHOD OF LIQUID DROPLET FORMATION AND TRANSPORT APPARATUS THEREFOR AND PARTICLE MANIPULATING APPARATUS

TECHNICAL FIELD

The present invention relates to techniques for liquid droplet formation and transport, and techniques for manipulation of transport objects such as particles and trace liquid samples, using liquid droplets.

BACKGROUND ART

With the genome project going forward, there has been an active move afoot to grasp a living organism at the DNA or protein level for examination for disease or understanding of the phenomena of life. To examine the status of gene expression is effective for the understanding of the phenomena of life or the investigation of the workings of genes. A probe array, namely, a DNA chip or a protein chip, having many DNA probes or protein probes partitioned according to the type of probe and immobilized on the surface of a solid body such as slide glass, has come into use as an effective method for examination of the status of gene expression. Chip making methods include a method that involves synthesizing a designed sequence of oligomers, base by base, with many compartmented cells, using photochemical reaction and lithography that is widely used in the semiconductor industry (Science 251, 767-773 (1991)), and a method that involves implanting plural types of probes, one by one, in compartments (Science 270, 467-470 (1995); and Nat. Biotechnol. 18, 438-441 (2000)).

With any of these methods, the fabrication of the chip requires the immobilization of the DNA probes or the protein probes on each array, or the base-by-base synthesis of the oligomers if specialized for the DNA probes; hence the fabrication takes time and effort, resulting in high costs. Also, the probes are generally mounted as liquid droplets on the surface of the solid body, which in turn involves problems in that there is compartment-to-compartment variation, that it is not easy to make varying combinations of the types of probes, and that manipulation is not easy for a user, and so on.

To solve the above problems, there has been a proposal of a probe array, namely, a particle array, having a collection of plural types of particles, which are prepared by immobilizing the DNA probes or the protein probes on the particles (Clinical Chemistry 43, 1749-1756 (1997); Nucleic Acids Research 30, e87 (2002); and Description in U.S. Pat. No. 6,023,540). The advantage of the probe array using the particles is that the probe array can be fabricated without particle-to-particle variation in probe density since a probe immobilization method utilizing chemical reaction in a solution can be employed.

For the DNA chip or the protein chip, a method that involves identifying the type of probe by any one of the point of oligomer formation and the point of probe spot is adopted. Meanwhile, for the probe array using the particles having the probes immobilized thereon, any one of a method using a color-coded particle for each probe (Clinical Chemistry 43, 1749-1756 (1997); and Description in U.S. Pat. No. 6,023, 540) and a method that involves identifying the type of probe by the sequence in which the particles are arranged in a capillary or in a micro fluid channel chip (Nucleic Acids Research 30, e87 (2002); Japanese Patent No. 3593525; and Japanese Patent Application Publication No. 2005-17224) is adopted.

For the conventional DNA chip or protein chip, for quantitative analysis of plural types of probes contained in a test sample, the reaction with the oligomers or the DNA or protein probes immobilized on the chip is allowed to occur, which takes from half a day to a day. On the other hand, for the probe array in which the particles are arranged in the capillary (Nucleic Acids Research 30 e87 (2002)), namely, the particle array, the test sample is forced to flow into and through the capillary. Since the particle array is more likely to enable a reduction in gene testing time as compared to the conventional method, it is measuring technology capable of not only being used in a relatively large-scale clinical test center but also being used for in-hospital or on-the-spot summary measurement, namely, Point of Care Testing (POCT). For example, the particle array can be expected to come into use as a means for quickly detecting a foreign gene that does not exist in a pathogenic microbe genome in itself, for an infection or bacteria test or the like for which a prompt diagnosis is urgently required.

For practical use of the particle array adopting the method that involves identifying the type of probe by the sequence in which the particles are arranged in the capillary (Nucleic Acids Research 30, e87 (2002)), the establishment of a method for selecting any given probe-immobilized particle in accordance with what purpose a test is used for and thereby arraying the particles as desired is essential, and thus, there have been proposals of several methods. For example, the methods include a method that involves effecting the flowing of the particles into the capillary, utilizing the flow of liquid, while performing individual control of the particles one by one (Japanese Patent Application Publication No. Hei 11-243997), and a method in which only one particle selected from among plural particles introduced in conjunction with a solvent is held on a sheet having formed therein a microscopic hole that admits only one particle, and the sheet is moved, with the particle held thereon, to the position of a channel formed in any one of the capillary and a flat sheet, whereby the particles are arranged (Japanese Patent Application Publication No. 2000-346842). However, these methods have a problem with reliability or usability because of often taking in the particles unsuccessfully under the influence of air bubbles.

Therefore, there has been a proposal of a method that involves using a particle capturing nozzle to capture, and manipulate, only one particle on its tip suction unit from within a container stocked with plural particles having probes of one and the same type immobilized thereon in conjunction with a solution (Japanese Patent No. 3593525; Japanese Patent Application Publication No. 2005-17224; and Analytical Chemistry 75, 3250-3255 (2003)). This method enables arraying the particles in intended sequence.

Patent Literature 1: Description in U.S. Pat. No. 6,023,540
Patent Literature 2: Japanese Patent Application Publication No. Hei 11-243997
Patent Literature 3: Japanese Patent Application Publication No. 2000-346842
Patent Literature 4: Japanese Patent No. 3593525
Patent Literature 5: Japanese Patent Application Publication No. 2005-17224
Non-patent Literature 1: Science 251, 767-773 (1991)
Non-patent Literature 2: Science 270, 467-470 (1995)
Non-patent Literature 3: Nat. Biotechnol. 18, 438-441 (2000)
Non-patent Literature 4: Clinical Chemistry 43, 1749-1756 (1997)

Non-patent Literature 5: Nucleic Acids Research 30, e87 (2002)

Non-patent Literature 6: Analytical Chemistry 75, 3250-3255 (2003)

DISCLOSURE OF THE INVENTION

Problems to be Solved by the Invention

With the particle capture method using the particle capturing nozzle, the fabrication of the particle array is accomplished by releasing the captured particle from the tip of the particle capturing nozzle, and introducing the released particle into the capillary or into the micro fluid channel chip. An airflow or a water flow has been heretofore used for the introduction of the particle; however, with a continuous flow of fluid, the released particle may not possibly follow the flow, and thus, there is seen a phenomenon in which the particle stays for a long time near an inlet of the capillary or an inlet of the micro fluid channel chip. This phenomenon causes not only a reduction in throughput in the fabrication of the particle array but also a problem in that the particles are arrayed in erroneous sequence unless there is provided a detecting means for sequentially checking whether the particles are arrayed. In particular, it has been shown that the frequency of occurrence of the above-mentioned problem increases in proportion to the number of particles arrayed in the capillary or in the fluid channel. This is due to the fact that a force required to suck in the particle becomes smaller with an increase in the number of particles arrayed because fluid resistance in the capillary or in the fluid channel becomes higher in proportion to the number of particles arrayed.

An object of the present invention is to provide a means and method for solving the foregoing problems. Another object of the present invention is to provide an apparatus for efficiently transporting or dispensing transport objects including not only particles but also liquid samples.

Means for Solving Problems

According to the present invention, a liquid droplet is formed in the inlet of the capillary or in the inlet of the micro fluid channel chip, a particle released from the tip of the particle capturing nozzle is enclosed in the liquid droplet, and the particle is introduced into the capillary or into the micro fluid channel chip. Once the particle is enclosed in the liquid droplet, the particle is transported with stability in conjunction with the liquid droplet, because of being hardly likely to be released from the liquid droplet to the outside under surface tension on a gas-liquid phase boundary.

Firstly, description will be given with regard to a liquid droplet formation and transport means. Two or more pipes for liquid transport (or liquid transport pipes) are prepared. For the sake of simplicity, description will be given here with regard to a system having only two liquid transport pipes prepared therein. The two liquid transport pipes will be hereinafter described as a first liquid transport pipe and a second liquid transport pipe, respectively. One end of the first liquid transport pipe is inserted into a liquid container, and a liquid in the container is sucked up and fed toward the other end of the first liquid transport pipe at a liquid feed velocity V1 by use of a pressure liquid feed pump. The other end is open to the atmosphere, and the liquid, after passing through the first liquid transport pipe, exits through the other end at a constant velocity. In early stages of exit, the liquid forms a spherical droplet (or liquid droplet) under surface tension. On the other hand, the second liquid transport pipe is linked at one end to a suction pump, which in turn forms a negative pressure in the second liquid transport pipe with a liquid feed velocity V2. When the liquid comes into contact with the other end of the second liquid transport pipe, the liquid can be sucked into and conveyed through the second liquid transport pipe.

When a liquid outlet at the other end of the first liquid transport pipe is brought near to a liquid inlet at the other end of the second liquid transport pipe, the liquid can be moved and transported from the first liquid transport pipe to the second liquid transport pipe, provided that the distance between the liquid outlet and the liquid inlet is such that the liquid droplet exiting through the liquid outlet reaches the liquid inlet rather than falls under the influence of gravity. The gap between the liquid outlet and the liquid inlet will be hereinafter described as an air gap. Here, discussion is made focusing on the liquid feed velocities V1 and V2. When the relationship between V1 and V2 is maintained so as to be V1<V2, the liquid droplet sucked into the second liquid transport pipe is sheared off in the air gap. Thereby, a continuous fluid supplied from the first liquid transport pipe forms the liquid droplet in the air gap, and forms an intermittent flow of the liquid and gas (or air) in the second liquid transport pipe.

Description will now be given with regard to a particle capturing means. The particle capturing means includes a particle accommodating container that accommodates a solution containing plural particles, a long, narrow particle capturing nozzle that captures the particle at the tip, a suction unit and a pressurization unit linked to the particle capturing nozzle, and an actuator for inserting the tip of the particle capturing nozzle into the solution in the container and withdrawing the nozzle from the solution. An opening at the tip of the particle capturing nozzle is smaller than the diameter of the particle. The particle capturing nozzle having at the tip the smaller opening than the particle diameter is inserted into the solution containing plural particles having biomolecular probes immobilized on the surfaces, and suction is exerted on the tip of the particle capturing nozzle. Then, the particle capturing nozzle holding one particle at the tip by suction is withdrawn from the solution in the container, and the particle is released through the application of pressure to the particle held by suction at the tip of the particle capturing nozzle.

A particle manipulating apparatus according to the present invention includes the liquid droplet formation and transport means and the particle capturing means previously described. Specifically, the particle manipulating apparatus includes a first liquid transport pipe; a first liquid feed means for supplying a liquid to the first liquid transport pipe; a second liquid transport pipe; a second liquid feed means for conveying the liquid by suction; a stage that holds plural containers that accommodate a solution containing plural particles; an actuator that effects movement of the stage; a particle capturing nozzle having at the tip a smaller opening than the diameter of the particle; an actuator that drives the particle capturing nozzle; a suction and pressurization means for forming a positive or negative pressure at the tip of the particle capturing nozzle; and a controller for controlling these.

The particle capturing nozzle is located in such a relative position that the nozzle moves through the air gap between the first and second liquid transport pipes so as not to come into contact with the first and second liquid transport pipes. The tip of the particle capturing nozzle captures the particle from a particle stock container located in an extension of a direction in which the particle capturing nozzle moves, through the driving of the suction unit; the tip of the nozzle is moved to the air gap; and thereafter, the particle captured at the tip of the particle capturing nozzle is released into the liquid droplet formed in the air gap, through the driving of the pressurization unit. The released particle is enclosed in the liquid droplet by coming into contact with the liquid droplet, and is transported into the second liquid transport pipe.

When the second liquid transport pipe is replaced by a capillary or a micro fluid channel chip for use as a particle array container, the particle enclosed in the liquid droplet can be reliably guided into the capillary or into the fluid channel for the fabrication of the particle array. Because of utilizing the surface tension on the gas-liquid phase boundary, this method enables transporting the particle into the capillary or the fluid channel, not depending on flow velocity at which the particle flows thereinto.

Also, the particle capturing means is replaced by a trace dispensing means for a liquid sample, and a liquid immiscible with the liquid sample is used as the liquid supplied by the liquid droplet formation and transport means. This enables application to transport, dispensing or the like for a trace liquid sample. Further, when the liquid droplet formation and transport means is used as a single unit, the means can be utilized as a trace dispenser characterized in that the volume of the liquid droplet can be controlled by controlling the length of the air gap between the first and second liquid transport pipes.

Advantageous Effect of the Invention

The present invention ensures that particles having biomolecules immobilized thereon, one by one, can be introduced into the particle array container and be arrayed therein, thus making it possible to fabricate particle arrays each formed of an array of plural different particles, with high efficiency at low manufacturing cost. Also, the use of the apparatus of the present invention enables the trace dispensing of the liquid sample, thus enabling simple manipulation of transport objects including not only particles but also liquids.

EXPLANATION OF REFERENCE NUMERALS

1 . . . liquid container, 2 . . . first liquid feed pump, 3 . . . first liquid transport pipe, 4 . . . second liquid transport pipe, 5 . . . liquid collecting container, 6 . . . suction pump, 7 . . . pure water, 8 . . . three-way valve, 9 . . . liquid outlet, 10 . . . liquid inlet, 11 . . . air gap, 12 . . . liquid droplet, 13 . . . liquid section, 14 . . . air section, 15 . . . second liquid feed pump, 16 . . . slide glass flat sheet, 17 . . . dispensed liquid droplet, 18 . . . first plate-shaped member, 19 . . . accommodating unit, 20 . . . particle accommodating plate, 21 . . . plate mounting jig, 22 . . . first motor-driven actuator, 23 . . . second motor-driven actuator, 24 . . . second plate-shaped member, 25 . . . particle capturing nozzle, 26 . . . particle capturing nozzle mounting jig, 27 . . . third motor-driven actuator, 28 . . . solenoid three-way valve, 29 . . . particle suction pump, 30 . . . particle release pressure pump, 31 . . . third liquid transport pipe, 32 . . . first socket, 33 . . . controller (computer), 34 . . . solution, 35 . . . particle, 36 . . . micro fluid channel chip, 37 . . . second liquid transport pipe, 38 . . . second liquid transport pipe, 39 . . . particle container, 40 . . . probe-immobilized particle, 41 . . . particle array container, 42 . . . second socket, 43 . . . single stranded DNA probe having sequence 1, 44 . . . single stranded DNA probe having sequence 2, 45 . . . single stranded target DNA having sequence 3, 46 . . . single stranded target DNA having sequence 4, 47 . . . 20 mM phosphate buffer, 48 . . . fluorescence microscope, 49 . . . Cy3 fluorescence, 50 . . . TexasRed fluorescence, 51 . . . oil droplet, 52 . . . liquid dispensing nozzle, 53 . . . trace liquid, 54 . . . detection cell liquid transport pipe, 55 . . . light source, 56 . . . detector, 57 . . . sample solution droplet, 58 . . . reagent solution droplet, 59 . . . mixed solution, 60 . . . valve

BEST MODE FOR CARRYING OUT THE INVENTION

Embodiments of the present invention will be described below with reference to the drawings.

First Embodiment

Referring to the first embodiment, description will be given with regard to a liquid droplet formation method and an intermittent fluid transport method of the present invention, based on an experiment in which pure water is used.

Figure 1:
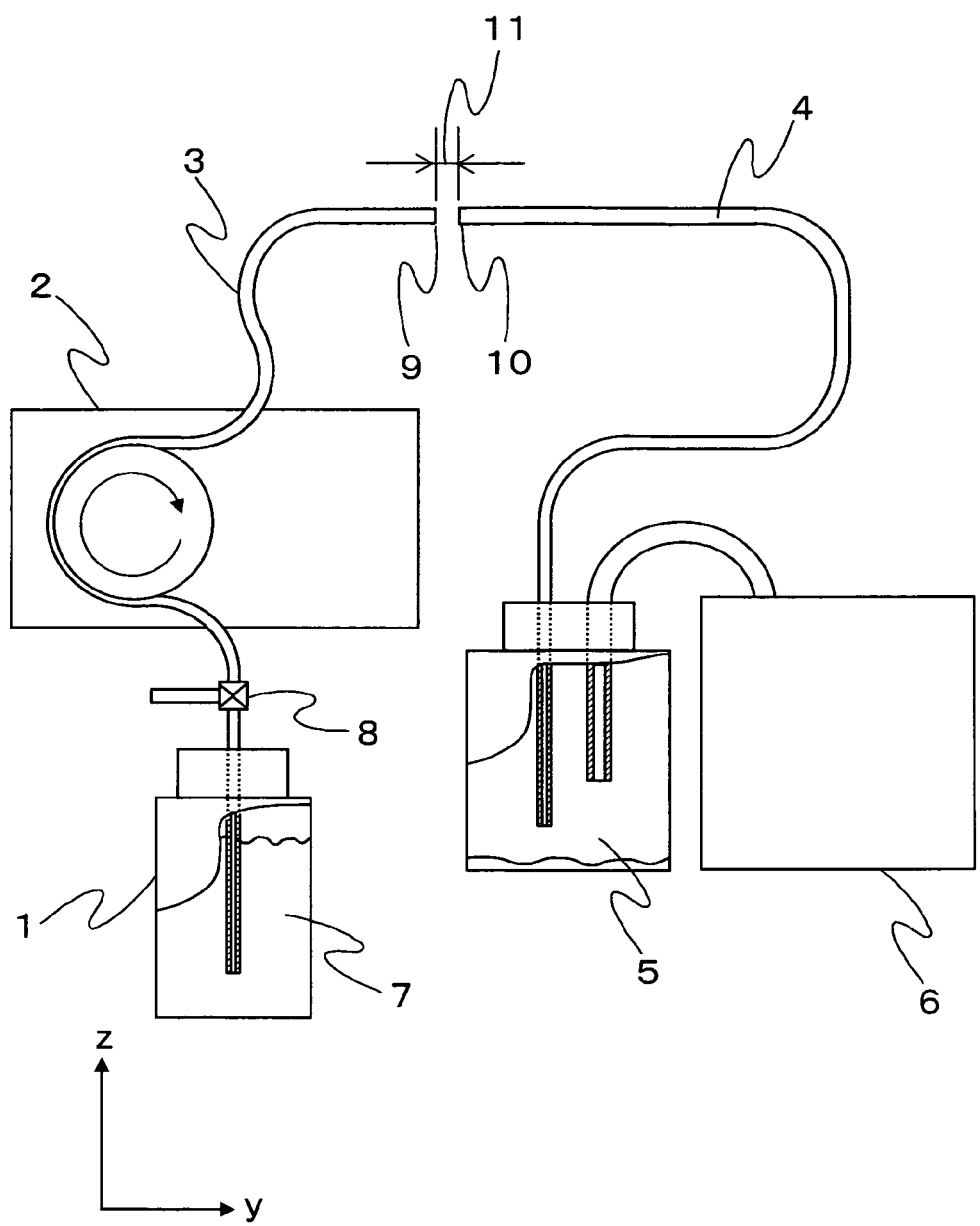
FIG. 1 is a schematic view showing a liquid droplet formation method and an intermittent fluid transport method of the present invention.

FIG. 1 is a general schematic view showing an experimental system for the liquid droplet formation method and the intermittent fluid transport method of the present invention. The experimental system includes a liquid container 1, a first liquid feed pump 2, a first liquid transport pipe 3, a second liquid transport pipe 4, a liquid collecting container 5, and a suction pump 6. The liquid container 1 is stocked with pure water 7. Also, a three-way valve 8 is interposed between the liquid container 1 and the first liquid feed pump 2. Here, a peristaltic pump is used as the first liquid feed pump 2; and an aspirator, as the suction pump 6. However, a diaphragm pump may be used in place of the peristaltic pump; or a peristaltic pump, a diaphragm pump, a rotary pump, an oil diffusion pump or the like, in place of the aspirator.

The first liquid transport pipe 3 and the second liquid transport pipe 4 lie coaxially along the y axis near their respective open ends and face each other at the respective open ends. The open end of the first liquid transport pipe 3 will be hereinafter described as a liquid outlet 9; and the open end of the second liquid transport pipe 4, as a liquid inlet 10. An air gap 11 that is the gap between the liquid outlet 9 and the liquid inlet 10 can vary between 0.0 mm and 2.0 mm.

Preferably, the inside diameters of the first liquid transport pipe 3 and the second liquid transport pipe 4 are around 0.01 mm to 1 mm. As will be described later, it is desirable that the pipes having a small inside diameter and a thin wall be used to reduce the volume of a liquid droplet formed in the air gap 11 or to make much of the volume reproducibility of the liquid droplet, or further, to set a variable range of volumes wide. In the first embodiment, the pipes having an inside diameter of 0.5 mm and an outside diameter of 1 mm are used.

The pure water 7 is fed to the first liquid transport pipe 3 by use of the first liquid feed pump 2 and is fed at a constant velocity V1. On the other hand, the second liquid transport pipe 4 is reduced in internal pressure by the order of 1 atmospheric pressure by means of the suction pump 6 that is the aspirator. At this time, a flow velocity V2 was set equal to 20 μL/sec. (V2=20 μL/sec.) In the first embodiment, V1 was set to vary between 0.1 μL/sec. and 20 μL/sec.

Figure 2:
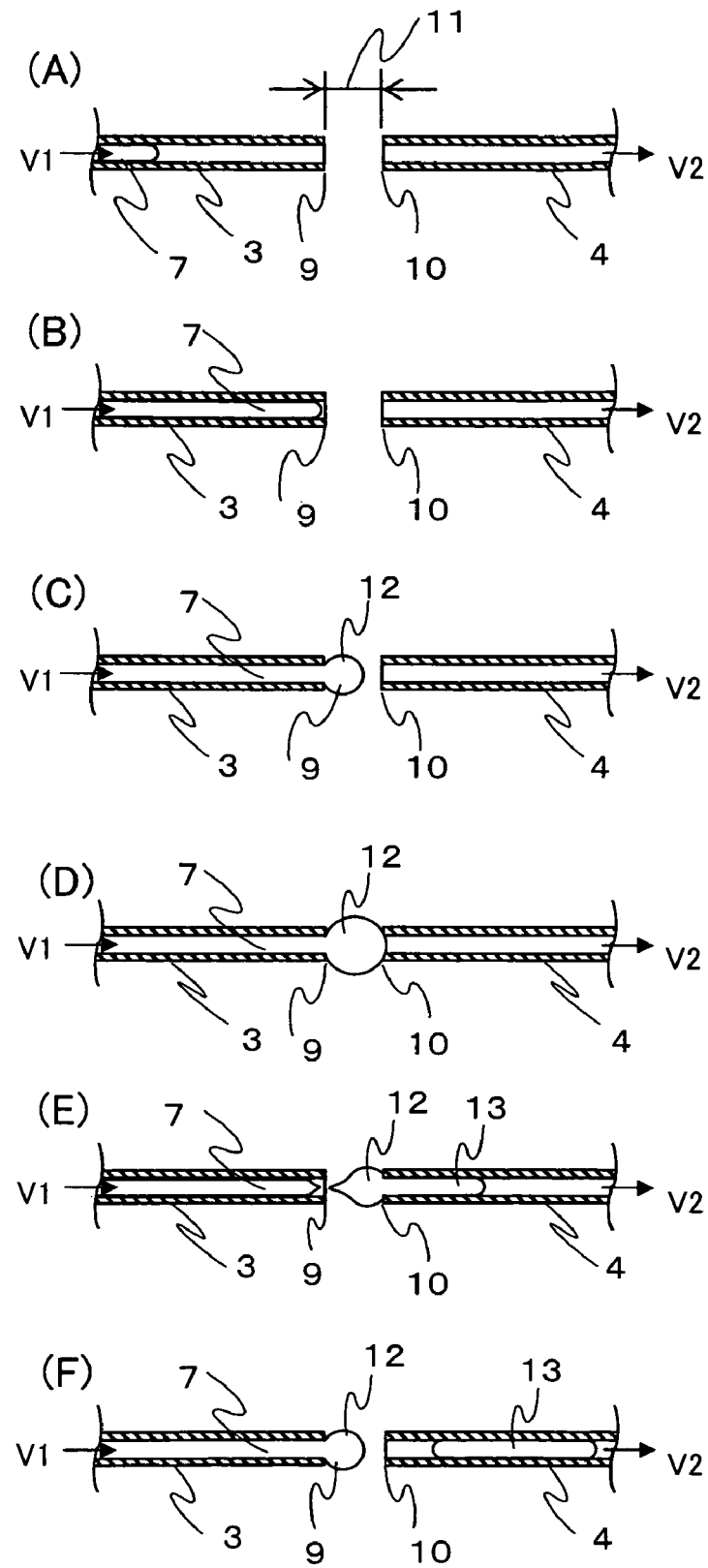
FIGS. 2(A) to 2(F) are schematic views illustrating the principle of liquid transport according to the present invention.

FIGS. 2(A) to 2(F) are schematic views illustrating the principle of liquid transport using the experimental system shown in FIG. 1. Here, conditions are that V1 is set equal to 5 μL/sec. (V1=5 μL/sec.), V2 is set equal to 20 μL/sec. (V2=20 μL/sec.), and the air gap is set equal to 1.5 mm. After being fed through the first liquid transport pipe 3 as shown in FIG. 2(A), the pure water 7 flows through the liquid outlet 9 and to the air gap 11 as shown in FIG. 2(B), and forms a liquid droplet 12 in the air gap 11 as shown in FIG. 2(C). The liquid droplet 12 expands spherically to the liquid inlet 10 of the second liquid transport pipe 4 as shown in FIG. 2(D), and is then sucked into the second liquid transport pipe 4 as shown in FIG. 2(E). V1<V2 leads to a great velocity gradient between the flow velocity near the liquid outlet 9 of the first liquid transport pipe 3 and the flow velocity near the liquid inlet 10 of the second liquid transport pipe 4. The liquid droplet 12 is subjected to a force acting to keep its spherical shape under surface tension, so that the greatest velocity gradient develops near the liquid outlet 9, which is the starting point of liquid droplet formation. Thereby, a shear force develops in a direction perpendicular to the direction of the flow of liquid. Thus, the liquid droplet is sucked and sheared off and is formed into a liquid section 13 as shown in FIG. 2(E). After that, it can be observed that an intermittent fluid of air and the pure water 7 results and flows through the second liquid transport pipe 4 as shown in FIG. 2(F). Under the condition that V1 is less than 20 μL/sec. (V1<20 μL/sec.), the same result as described with reference to FIGS. 2(A) to 2(F) is obtained, and the rate of liquid droplet formation rises in proportion to the flow velocity. The size of the liquid droplet 12 is controlled by the length of the air gap 11, so that the liquid section 13 in substantially a fixed amount is formed in the second liquid transport pipe 4.

Figure 3:
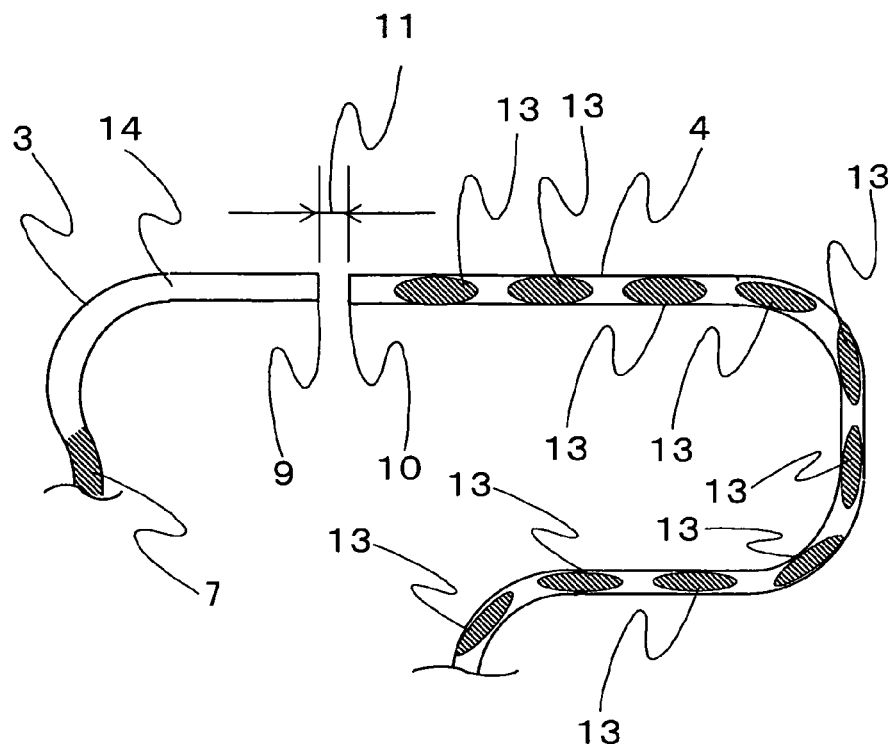
FIG. 3 is a schematic view showing the result that ten liquid sections each having a liquid volume of 2 μL are formed in a second liquid transport pipe.

FIG. 3 is a schematic view showing an instance where an air section 14 is forced into the first liquid transport pipe 3 through the switching of the three-way valve 8 at a given time, using the experimental system shown in FIG. 1. Here, conditions are that V1 is set equal to 5 μL/sec. (V1=5 μL/sec.), V2 is set equal to 20 μL/sec. (V2=20 μL/sec.), and the air gap 11 is set equal to 1.5 mm. The insertion of the air section 14 under timing control enables not only keeping constant the liquid volume of the liquid section 13 of the pure water 7 described with reference to FIGS. 2(A) to 2(F), but also controlling the number of liquid sections 13. FIG. 3 is the schematic view showing the result that ten liquid sections 13 each having a liquid volume of 2 μL are formed, in an instance where about 20 μL of the pure water 7 is sucked up by the first liquid feed pump 2 and thereafter the three-way valve 8 is switched to the air side.

Figure 4:
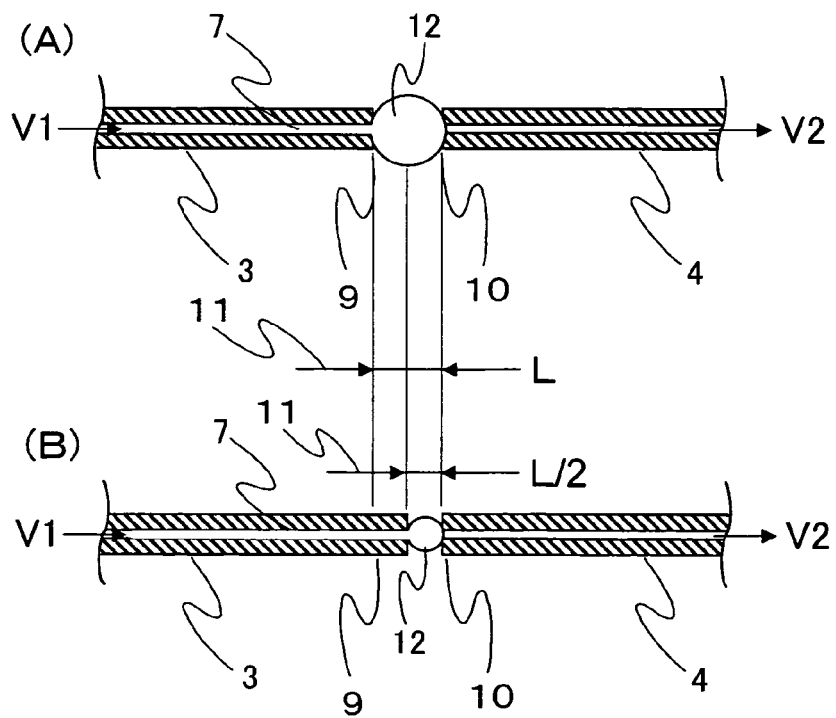
FIGS. 4(A) and 4(B) are schematic views showing an example of a method for controlling the size of a liquid droplet to be formed in an air gap.

FIGS. 4(A) and 4(B) are schematic views showing an example of a method for controlling the size of the liquid droplet 12 and thereby controlling the liquid volume of the liquid section 13. Controlling the length of the air gap 11 makes it possible to arbitrarily vary the diameter of a sphere of the liquid droplet 12, that is, an aliquot volume of the liquid droplet 12 or the liquid section 13. FIG. 4(A) shows a situation where the length of the air gap 11 is set to 1 mm to form 4 μL of the liquid droplet in the air gap 11. FIG. 4(B) shows a situation where the length of the air gap 11 shown in FIG. 4(A) is reduced by half. Reducing the air gap by half makes it possible to form in the air gap 11 0.5 μL of the liquid droplet 12, that is, the liquid droplet 12, the liquid volume of which is $\frac{1}{2}^3$ of the liquid volume shown in FIG. 4(A). If the air gap is equal to or less than 2 mm, the liquid droplet 12 of the pure water 7 or a buffer solution has a completely spherical form without being affected by the influence of gravity, under strong surface tension, which makes it possible to achieve a precise, fixed, aliquot quantity. Thereby, a preintended precise liquid volume of the liquid section 13 can be manipulated into the second liquid transport pipe 4. On the other hand, if the air gap is more than 2 mm, the liquid droplet 12 has the form of an oval sphere hanging down in the direction of gravity, rather than the completely spherical form, under the influence of gravity. The oval sphere is sensitive to vibration or airflow, which makes it difficult to reproduce the shape of the liquid droplet 12, that is, the volume thereof. In the worst case, the liquid droplet 12 falls rather than expands to the liquid inlet 10 of the second liquid transport pipe 4. Preferably, the air gap 11 is set to 2 mm or less, which keeps a completely spherical configuration, since the air gap more than 2 mm causes variations in the aliquot quantity as mentioned above. Preferably, the length of the air gap 11 is controlled to 0.5 mm or less for other liquids, a biological sample such as serum, or oil.

As previously mentioned, the use of the pipes having the small inside diameter achieves an improvement in the reproducibility of the aliquot liquid volume. The use of such pipes achieves accurate reproduction of which part of the liquid droplet 12 shearing takes place in, since the liquid is subjected to a great force by the velocity gradient near the liquid outlet 9, or equivalently, the liquid can be cut off even under a weak force. Also, for achieving a trace aliquot quantity of liquid, the use of such pipes is preferable since the incoming liquid has a small cross-sectional area. However, it is desirable that the thin-walled pipes having a small outside diameter be used in order to prevent the liquid from being adsorbed on and spreading over the cross sections of the pipes. For the use of the pipes having a heavy wall thickness, water-repellent coating is applied to the cross sections of the pipes. The use of the first liquid transport pipe 3 and the second liquid transport pipe 4 having an inside diameter of 0.01 mm makes it possible to satisfactorily achieve an aliquot quantity of liquid lying between 500 μL and 5 μL.

Figure 5:
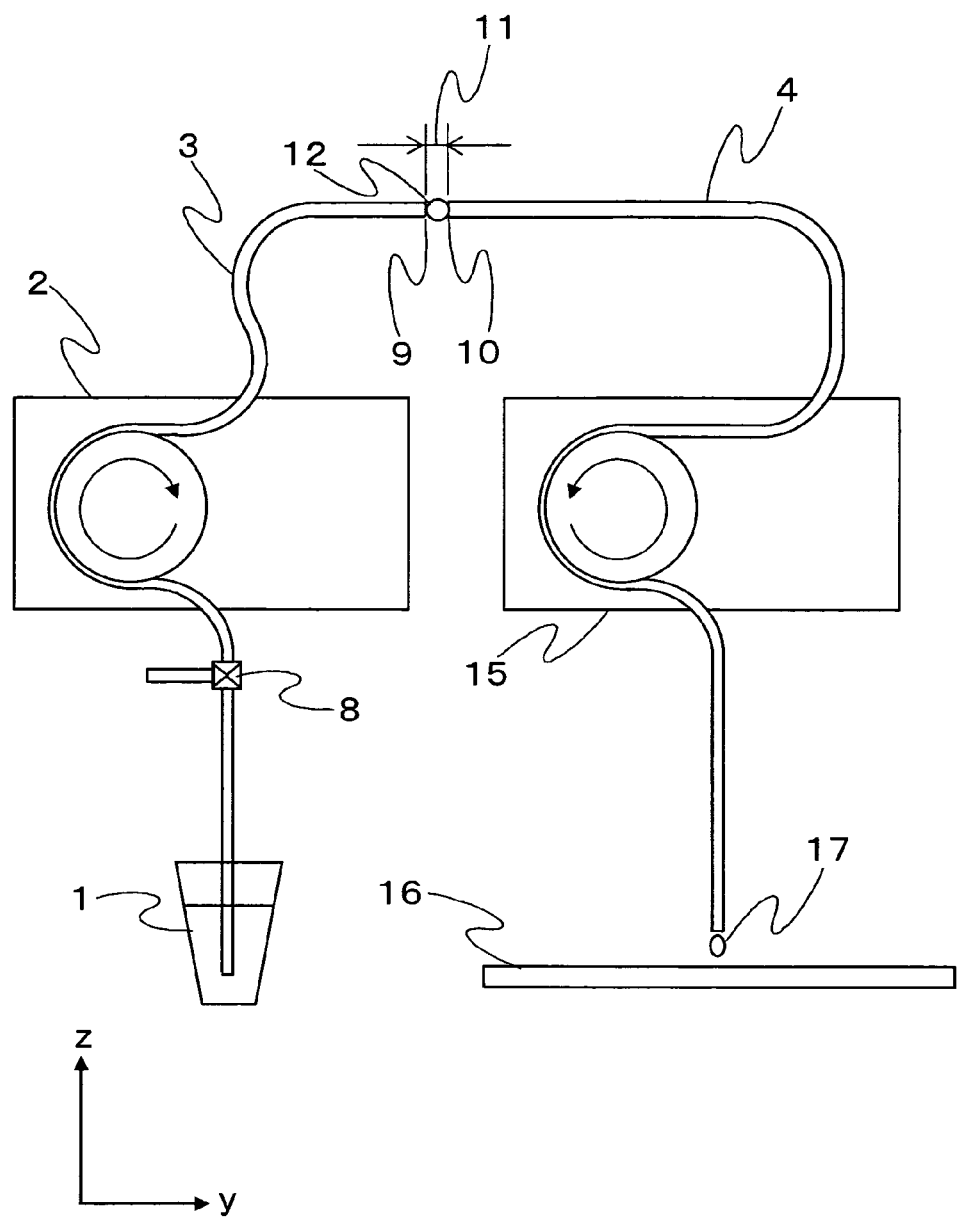
FIG. 5 is a schematic view showing a trace dispensing apparatus as an example of application of the present invention.

FIG. 5 is a schematic view showing an example of a liquid droplet formation and transport means described with reference to FIGS. 1 to 4(B), as applied to trace dispensing. A second liquid feed pump 15 such as a peristaltic pump or a diaphragm pump is used in place of the suction pump 6, as the pump for forming a negative pressure in the second liquid transport pipe 4. Also, a chamber may be prepared by surrounding the air gap and pressurized for use as the liquid feed pump. The use of any one of these alternative pumps makes it possible to drop the dispensed liquid section 13 on a reactor or a slide glass flat sheet 16, or further, on a membrane. FIG. 5 shows a situation where the liquid droplet is being dropped onto the slide glass flat sheet 16. The fabrication of a DNA chip or a protein chip can be accomplished by preparing DNA probes or protein probes, and dropping a dispensed liquid droplet 17 that has passed as the liquid section 13 through the second liquid transport pipe 4, while controlling the position of the slide glass flat sheet 16 by means of an actuator.

The means and method according to the first embodiment described above with reference to FIGS. 1 to 5 can be used as a trace dispenser for a micro titer plate, a trace spotter for the DNA chip or the protein chip, or further, a spotter for a pretreatment slide for a matrix-assisted laser desorption ionization (MALDI)—mass analysis system for protein.

Second Embodiment

Referring to the second embodiment, description will be given with regard to a particle manipulating apparatus and a method therefor. Here covered is a method for fabricating a particle array in the second liquid transport pipe 4. Description will be given with regard to an instance where plural types of particles are prepared by having a fixed particle diameter and immobilizing biological molecular probes on the surfaces of the particles and the particles are arrayed in a line in predefined sequence in the second liquid transport pipe 4, with reference to a view of apparatus configuration and based on the principle of operation.

Figure 6:
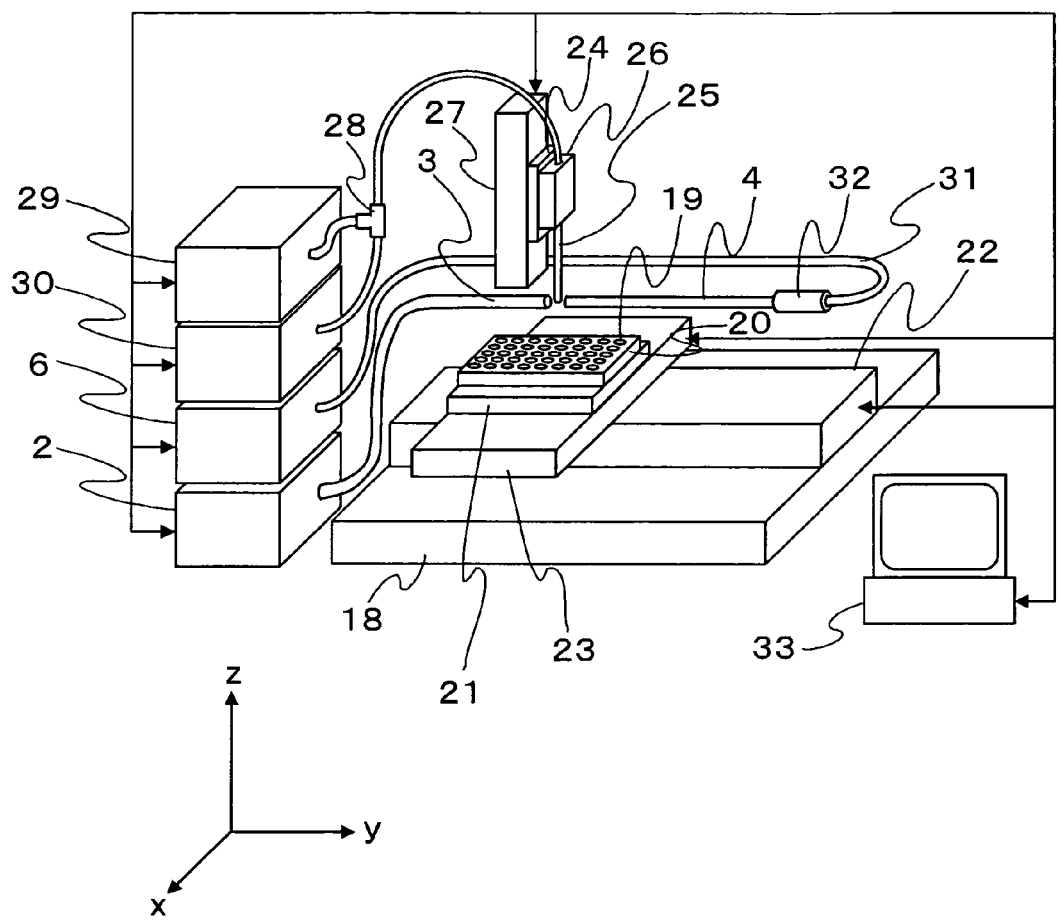
FIG. 6 is a schematic view showing a particle manipulating apparatus of the present invention.

FIG. 6 is a schematic view showing an example of the particle manipulating apparatus of the present invention. A particle accommodating plate 20 having plural accommodating units 19 holding particles having immobilized thereon biological probes bonded to biomolecules such as DNA, RNA or protein, and a plate mounting jig 21 are mounted on a first plate-shaped member 18 along with a first motor-driven actuator 22 and a second motor-driven actuator 23.

For the sake of simplicity, FIG. 6 shows an instance where the particle accommodating plate 20 having the accommodating units 19, the total number of which is forty, that is, five in the direction of the x axis by eight in the direction of the y axis (5×8=40), is mounted; however, it is preferable that a micro titer plate with 96 holes (8×12) or a micro titer plate with 384 holes (16×24) be used as the particle accommodating plate 20. The position of the particle accommodating plate 20 is controlled by the first motor-driven actuator 22 that is movable in the direction of the y axis and the second motor-driven actuator 23 that is movable in the direction of the x axis. The plate mounting jig 21 is provided with an oscillator capable of arbitrarily controlling amplitude and an oscillation frequency.

A particle capturing nozzle 25 having an inside diameter that permits the nozzle to suck in and hold only one particle at the tip, and a particle capturing nozzle mounting jig 26 are fixed on a second plate-shaped member 24 along with a third motor-driven actuator 27.

In order for the particle capturing nozzle 25 to suck in and hold only one particle at the tip, ID can be set to satisfy the following relationship: ID<R, and OD can be set to satisfy the following relationship: R≦OD<2R, where R denotes the particle diameter; ID, the inside diameter of the particle capturing nozzle 25; and OD, the outside diameter of the particle capturing nozzle 25. If the particle diameter is 100 μm, it is appropriate that a capillary made of glass or stainless steel, having an inside diameter of 50 μm and an outside diameter of 100 μm or 150 μm, is used as the particle capturing nozzle 25. However, the particle capturing nozzle 25, the outside diameter of which is two or more times the particle diameter, is often used to manipulate small particles of the order of 10 μm. In this case, the oscillator of the plate mounting jig 21 previously mentioned is used. On that occasion, oscillation having a frequency of 20 Hz or more and an amplitude of 0.1 mm or more can be applied in the direction of the x axis and in the direction of the y axis shown in FIG. 6.

One end of the particle capturing nozzle 25 is linked via a solenoid three-way valve 28 to a particle suction pump 29 and a particle release pressure pump 30. The first liquid feed pump 2, the first liquid transport pipe 3, the second liquid transport pipe 4 and the suction pump 6 are the same as described with reference to FIG. 1. The first liquid feed pump 2 feeds to the first liquid transport pipe 3 the pure water with which the liquid container 1 (not shown in FIG. 6) is stocked.

As distinct from the configuration of the liquid droplet formation and transport means described with reference to FIG. 1, the second liquid transport pipe 4 is connected via a first socket 32 to a third liquid transport pipe 31, and the third liquid transport pipe 31 is linked to the suction pump 6. Desirably, the first socket 32 is a member capable of being handled integrally with the second liquid transport pipe 4, and has a rectangular hole having a side that is smaller than the inside diameter of the second liquid transport pipe 4 and is a little smaller than the diameter of the particle to be manipulated. More preferably, the first socket 32 is uneven in cross-sectional configuration. This eliminates the particle getting caught in the first socket 32, thus making it possible to lower fluid resistance. Also, the interposing of the first socket 32 between the second liquid transport pipe 4 and the third liquid transport pipe 31 enables holding the particle within the second liquid transport pipe 4.

As for the second liquid transport pipe 4, it is necessary to use the second liquid transport pipe 4 whose inside diameter satisfies the following relationship: $R < ID < 2R$, where $R$ denotes the particle diameter; and ID, the inside diameter of the second liquid transport pipe 4. For example, if the particle diameter R is 0.1 mm, the inside diameter ID of the second liquid transport pipe 4 can be set to the order of 0.15 mm, and a commercially available glass capillary having an inside diameter of 0.15 mm and an outside diameter of 0.38 mm, for example, is generally used. Here, the reason for using a glass material for the second liquid transport pipe 4 is that self-fluorescence is the minimum over a wide range of wavelengths on the occasion of fluorescence analysis for an assay using the particle array. Of course, the material may be changed according to what purpose the pipe is used for. For example, a transparent plastic tube may be used for analysis utilizing bioluminescence or chemiluminescence. As for the fluorescence analysis for the assay using the particle array, description thereof will be given in a fifth embodiment.

The first motor-driven actuator 22 that acts as a driver for the overall system shown in FIG. 6, the second motor-driven actuator 23, the third motor-driven actuator 27, the solenoid three-way valve 28, the particle suction pump 29, the particle release pressure pump 30, the first liquid feed pump 2, the suction pump 6, and the oscillator of the plate mounting jig 21 are subject to centralized control by a controller (a computer) 33.

FIGS. 7(A) to 7(G) are schematic cross-sectional views showing a process for capturing one, namely a particle 35, of plural particles accommodated in conjunction with a solution 34 in the accommodating unit 19, using the particle manipulating apparatus of the present invention shown in FIG. 6. Here, conditions are that V1 is set equal to 5 μL/sec. (V1=5 L/sec.), V2 is set equal to 20 μL/sec. (V2=20 μL/sec.), the air gap is set equal to 1 mm, the diameter of the particle 35 is set equal to 100 μm, the inside diameter of the particle capturing nozzle 25 is set equal to 50 μm, and the outside diameter thereof is set equal to 100 μm. Also, the inside diameters of the first liquid transport pipe 3 and the second liquid transport pipe 4 are set equal to 150 μm, and the outside diameters thereof are set equal to 500 μm. Incidentally, the solution 34 is pure water. Of course, pure water, a buffer solution, alcohol or the like may be used as the solution 34. Here, oscillation is not applied to the particle accommodating plate 20 for the sake of simplicity of explanation.

Figure 7A:
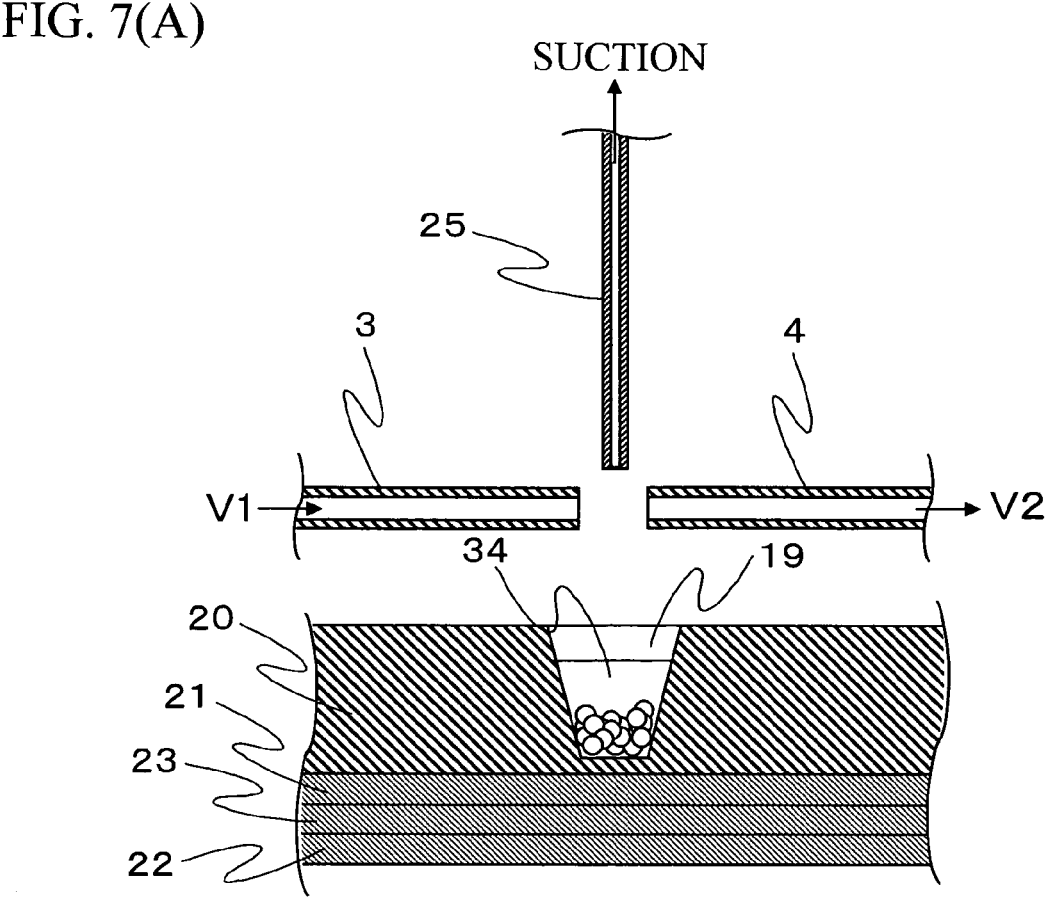
FIG. 7(A) is a schematic view showing an instant immediately before a particle capturing nozzle is just about to be inserted into a target accommodating unit.

FIG. 7(A) shows a situation where the particle accommodating plate 20 is moved by the first motor-driven actuator 22 and the second motor-driven actuator 23 so that an opening of the accommodating unit 19 holding the target particle 35 is positioned facing an opening of the particle capturing nozzle 25 in the direction of the z axis. The particle capturing nozzle 25 is just about to be inserted into the target accommodating unit 19. At this point, the solenoid three-way valve 28 is driven to subject the tip of the particle capturing nozzle 25 to a negative pressure, in order that the particle capturing nozzle 25 is linked to the particle suction pump 29.

Figure 7B:
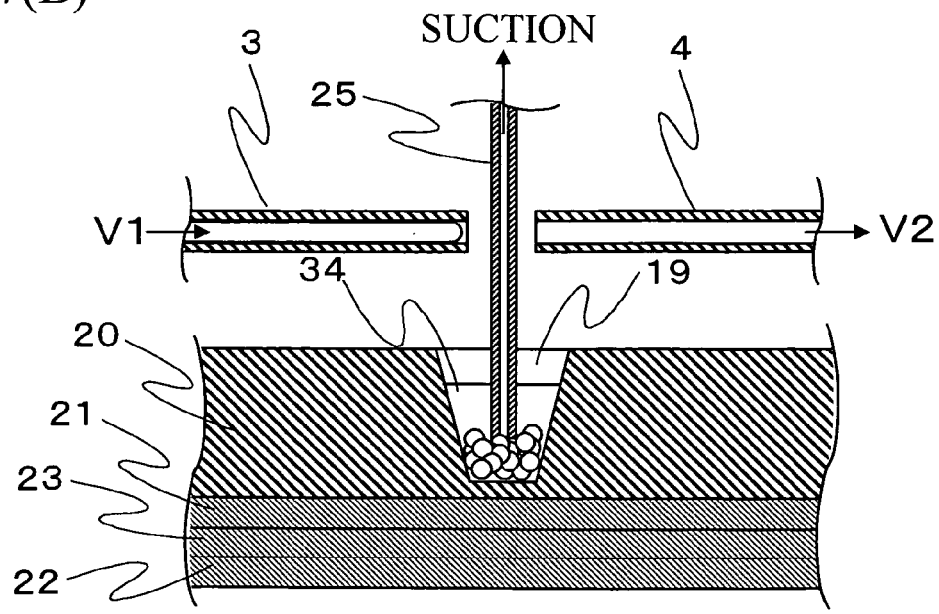
FIG. 7(B) is a schematic view showing a situation where the particle capturing nozzle having a negative pressure formed therein is inserted into the accommodating unit.

FIG. 7(B) shows a situation where under control of the third motor-driven actuator 27, the particle capturing nozzle mounting jig 26 moves downward in the direction of the z axis, so that a lower end of the particle capturing nozzle 25 having the negative pressure formed therein is inserted inwardly into the accommodating unit 19. The particle capturing nozzle 25 should be inserted to such an extent that its end face is in contact with the bottom of the accommodating unit 19. This is due to the fact that if the amount of the particles 35 accommodated is small, the tip of the particle capturing nozzle 25 cannot come into contact with the particle 35 and is thus reduced in capture efficiency. In this case, oscillation is applied to the particle accommodating plate 20 to improve the particle capture efficiency of the particle capturing nozzle.

The liquid droplet formation method and the liquid transport method are as described with reference to FIGS. 2(A) to 2(F). Of course, the air section 14 described with reference to FIG. 3 may be inserted at an appropriate time, while the particle capturing nozzle 25 moves through the gap between the first liquid transport pipe 3 and the second liquid transport pipe 4; however, if the particle capturing nozzle 25 is sufficiently small relative to the liquid droplet to be formed, the insertion of the air section 14 is not required. The reason is that the particle capturing nozzle 25 does not prevent the liquid droplet 12 from expanding to the second liquid transport pipe 4, if the following condition is satisfied: $R_0/R_1 \geq 5$, where $R_0$ denotes the diameter of the liquid droplet 12; and $R_1$, the outside diameter of the particle capturing nozzle 25. On the other hand, if the following condition is satisfied: $R_0/R_1 < 5$, the particle capturing nozzle 25 prevents the liquid droplet 12 from expanding to the second liquid transport pipe 4, and therefore, the insertion of the air section 14 is required. This description illustrates particle manipulation for the continuous formation of the liquid droplets for the sake of simplicity.

Figure 7C:
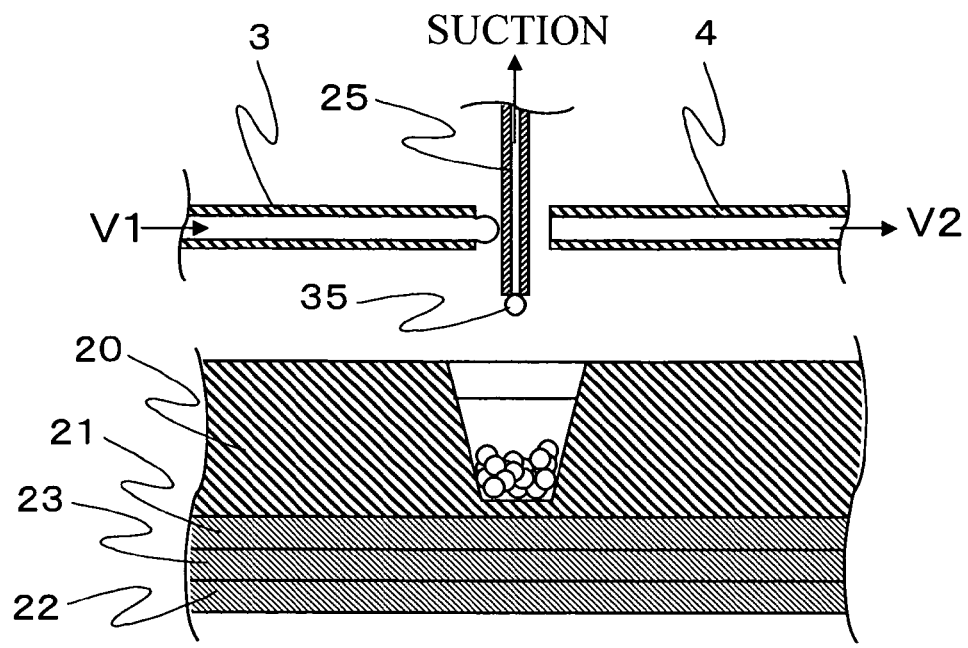
FIG. 7(C) is a schematic view showing a situation where the particle capturing nozzle holds only one particle at the tip.

FIG. 7(C) shows a situation where the tip of the particle capturing nozzle 25 is completely withdrawn from the solution 34 in the accommodating unit 19 into the atmosphere. At this time, the particle capturing nozzle 25 holds only one particle 35 at the tip. A physical phenomenon described below (not shown) occurs between steps shown in FIGS. 7(B) and 7(C).

While the particle capturing nozzle 25 is moved from the position shown in FIG. 7(B) to the position shown in FIG. 7(C), a liquid bridged structure or static electricity is produced between the particle capturing nozzle 25 and the particles 35 in the solution 34, and thus, the undesired particles 35 are adsorbed on an outer wall of the particle capturing nozzle 25. However, the undesired particles 35 fall off into the solution 34 under surface tension acting on a gas-liquid phase boundary between the solution 34 and the atmosphere, and thus, when the particle capturing nozzle 25 is exposed to the atmosphere, the particle capturing nozzle 25 sucks in and holds only one particle 35 at the opening.

Figure 7D:
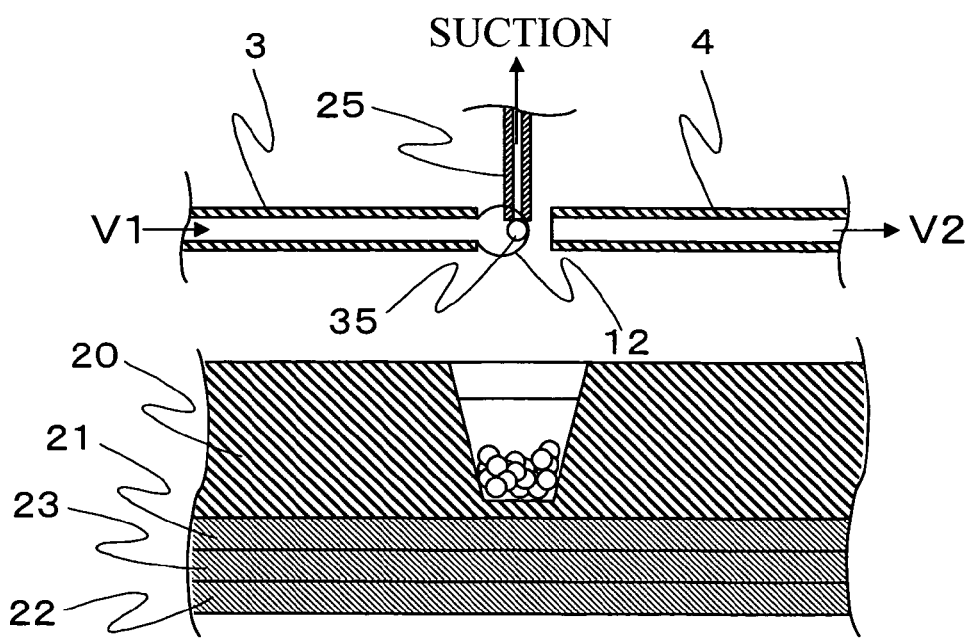
FIG. 7(D) is a schematic view showing an instant immediately before the particle is released into the liquid droplet.
Figure 7E:
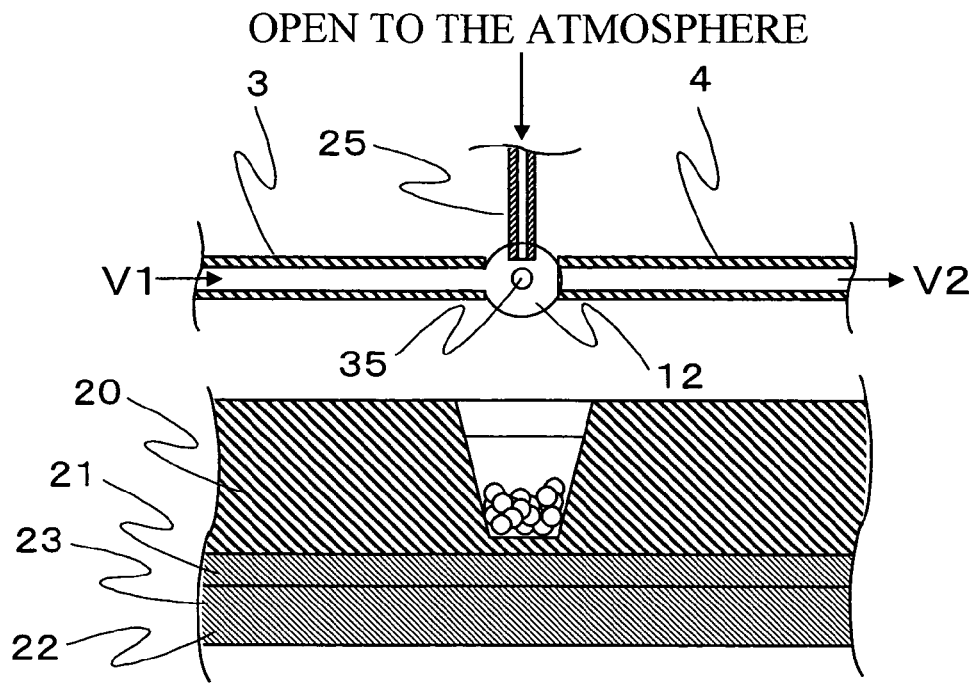
FIG. 7(E) is a schematic view showing a situation where the particle is released into the liquid droplet.

FIGS. 7(D) and 7(E) are schematic views showing the instant at which the captured particle 35 is released into the liquid droplet formed in the air gap 11. In a situation shown in FIG. 7(D), the particle capturing nozzle 25 remains sucking, and thus, the pure water 7 of the liquid droplet 12 partially flows also into the nozzle toward the particle suction pump. In FIG. 7(E), the switching of the solenoid three-way valve 28 leads to the particle capturing nozzle 25 being linked to the particle release pressure pump 30, thus making the inside of the particle capturing nozzle 25 open to the atmosphere. Thereby, the particle 35 is released into the liquid droplet 12. Making the nozzle open to the atmosphere is synchronized to a liquid droplet formation interval by use of the controller (the computer) 33. A vision sensor or CCD camera or a line sensor can be used as a detecting means for providing synchronization. Making the nozzle open to the atmosphere is effected by sending a signal to the controller 33 while making a direct observation of the liquid droplet. Alternatively, making the nozzle open to the atmosphere may be effected by monitoring an interval between the liquid sections flowing through the second liquid transport pipe 4; determining regularity in the interval; sending data on the regularity to the controller 33; and providing appropriate timing to make the nozzle open to the atmosphere. Also, the application of pressure by the particle release pressure pump 30 is for the purpose of making the nozzle open to the atmosphere, rather than for the purpose of causing the particle 35 to move off under pressure. It is therefore required that a pressure for application and a pressure application time be preset, allowing for the length of piping between the particle capturing nozzle 25 and the particle release pressure pump 30 and the inside diameter of the piping.

Figure 7F:
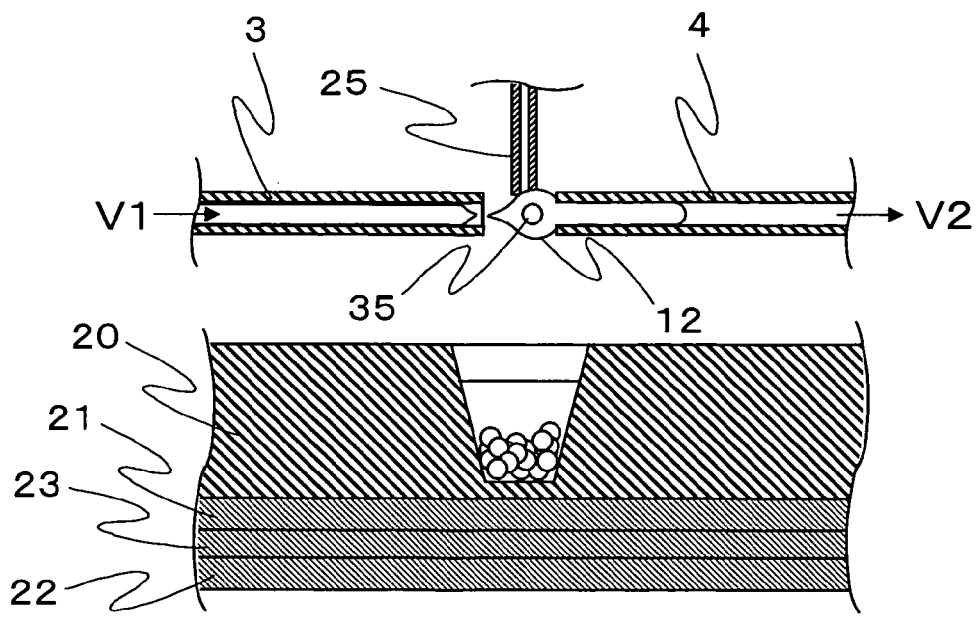
FIG. 7(F) is a schematic view showing a situation where the particle enclosed in the liquid droplet is transported into the second liquid transport pipe.
Figure 7G:
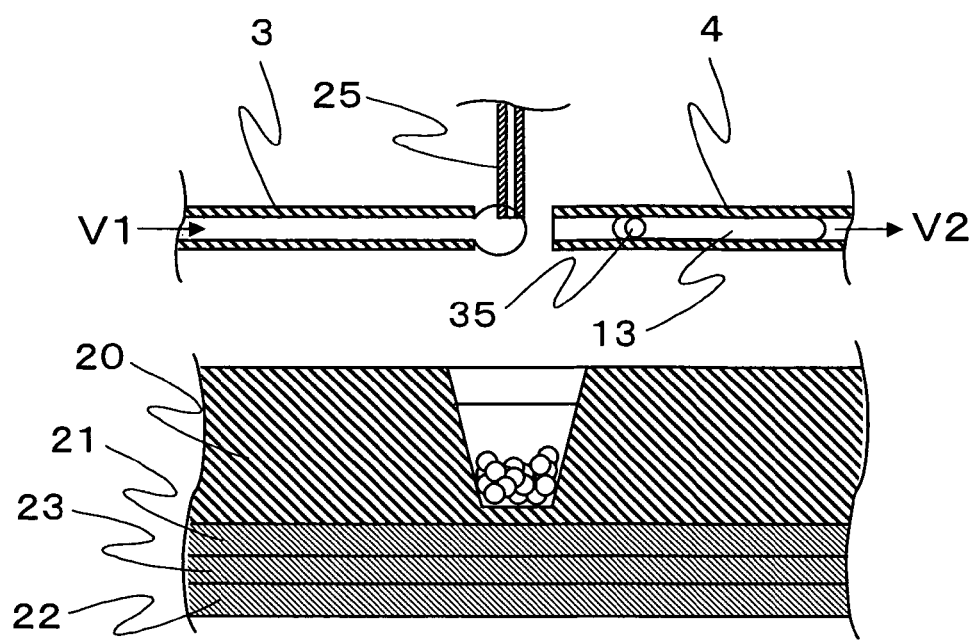
FIG. 7(G) is a schematic view showing a situation where the particle enclosed in the liquid section is transported.

FIGS. 7(F) and 7(G) are schematic views showing a situation where the particle 35 enclosed in the liquid droplet 12 is transported into the second liquid transport pipe 4. The enclosed particle 35 is not released to the outside but introduced with stability into the second liquid transport pipe 4 under surface tension on the liquid droplet 12 and under internal pressure therein. In FIG. 7(G), the particle 35 is shown as being conveyed in conjunction with the liquid section 13 through the second liquid transport pipe 4.

The process of operation described with reference to FIGS. 7(A) to 7(G) ensures that the particles 35, one by one, can be individually manipulated and introduced into the second liquid transport pipe 4. The fabrication of the particle array can be accomplished by doing the process for individual manipulation of the particles 35 one by one, for each of the accommodating units 19 of the particle accommodating plate 20. The use of the micro titer plate with 384 holes enables the fabrication of 384 types of particle arrays for multi-item testing.

Figure 8:
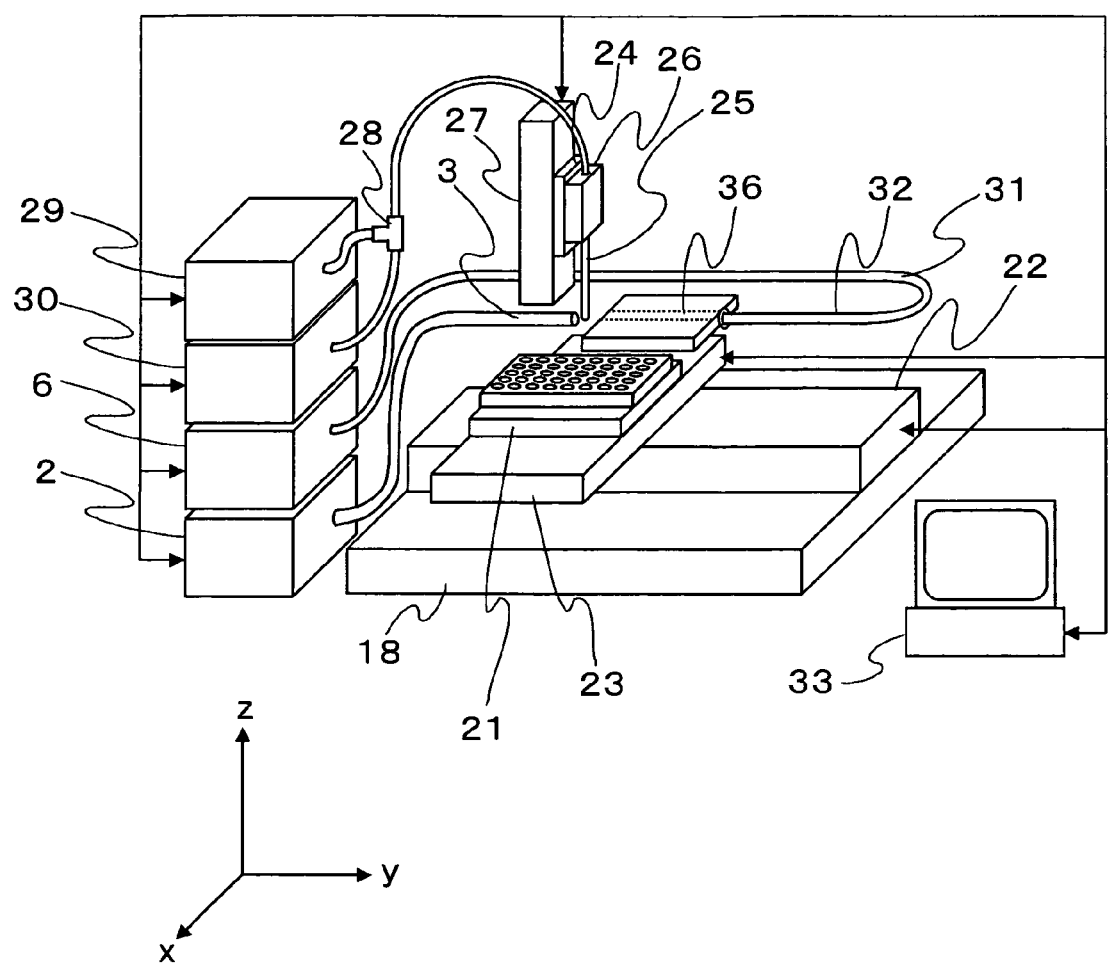
FIG. 8 is a schematic view of the particle manipulating apparatus of the present invention in which a micro fluid channel chip is used as a particle array container.

FIG. 8 shows an illustrative instance where a micro fluid channel chip 36 is used as a replacement as a particle array container that acts as the second liquid transport pipe 4. Thereby, the method described with reference to FIGS. 7(A) to 7(G) can be likewise employed to fabricate the particle array in the micro fluid channel chip 36. The micro fluid channel chip 36, the details of which are not shown, refers generally to that fabricated by tightly bonding raw slide glass to slide glass made of quartz glass or Pyrex (which is a registered trade mark) or a substrate made of PDMS (polydimethylsiloxane), having a particle array fluid channel formed on the surface by means of patterning using wet etching or the like. The particle array fluid channel has a cross-sectional area that admits only one particle, and is provided with a weir for preventing the particle from flowing out, which is disposed in a distal end region of the array fluid channel toward the third liquid transport pipe 31. Clearance is provided between the weir and a fluid channel wall of the particle array fluid channel so as to avoid a blockage in the fluid channel.

Third Embodiment

Figure 9:
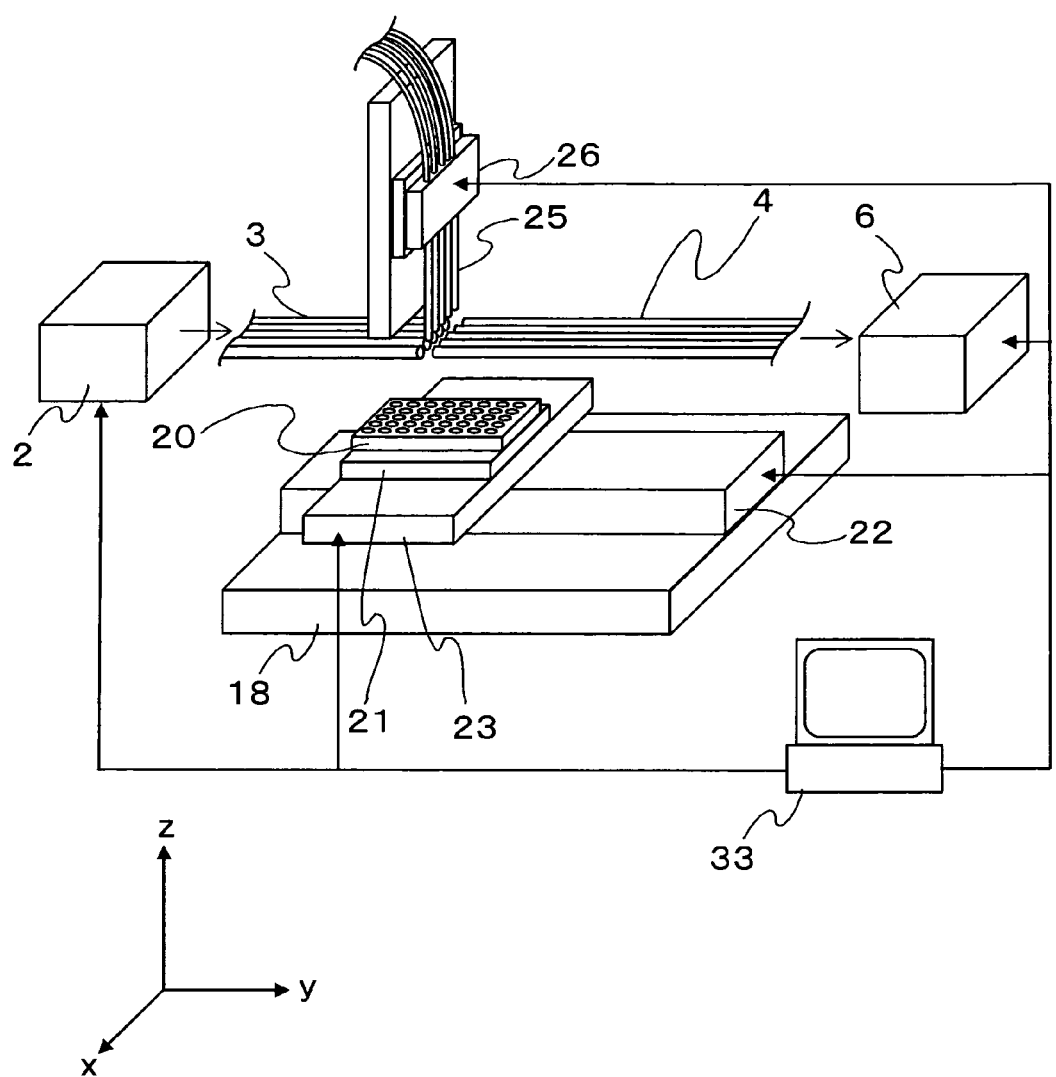
FIG. 9 is a schematic view showing an example of apparatus configuration of the present invention having a parallel arrangement of particle manipulating means.
Figure 10:
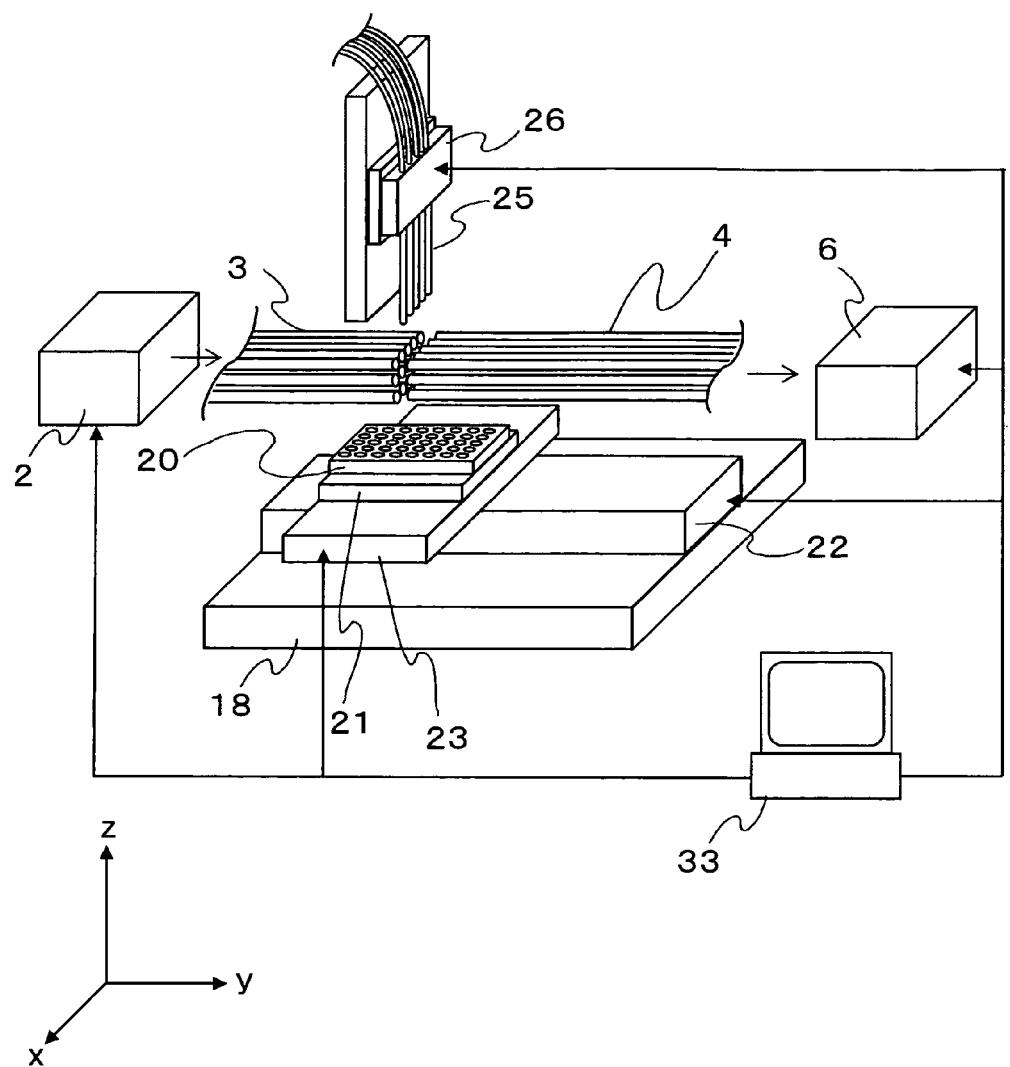
FIG. 10 is a schematic view showing an example of apparatus configuration of the present invention having a parallel arrangement of particle manipulating means.

FIGS. 9 and 10 show two examples of apparatus configuration having a parallel arrangement of particle manipulating means described with reference to FIG. 6 and FIGS. 7(A) to 7(G).

In FIG. 9, the particle capturing nozzles 25, the number of which is five, are mounted to the particle capturing nozzle mounting jig 26. The particle capturing nozzles 25 are arranged in side by side relation parallel to the x-z plane at given spaced intervals in the direction of the x axis. Also, the openings of the particle capturing nozzles 25 are all in the same position in the direction of the z axis. Also installed are the first liquid transport pipes 3 and the second liquid transport pipes 4, the numbers of which are likewise each five. The first liquid transport pipes 3 and the second liquid transport pipes 4 are arranged in side by side relation parallel to the x-y plane at given spaced intervals in the direction of the x axis. Also, the openings of the first and second liquid transport pipes 3 and 4 are all in the same position in the direction of the y axis. The five particle capturing nozzles 25, the five first liquid transport pipes 3 and the five second liquid transport pipes 4, one each, are disposed in such a manner as to lie in the same y-z plane. Extensions of the central axes of the five particle capturing nozzles 25 correspond to the positions of the air gaps 11, respectively, and to the positions of the openings of the five accommodating units 19, respectively, of the particle accommodating plate 20.

Figure 11:
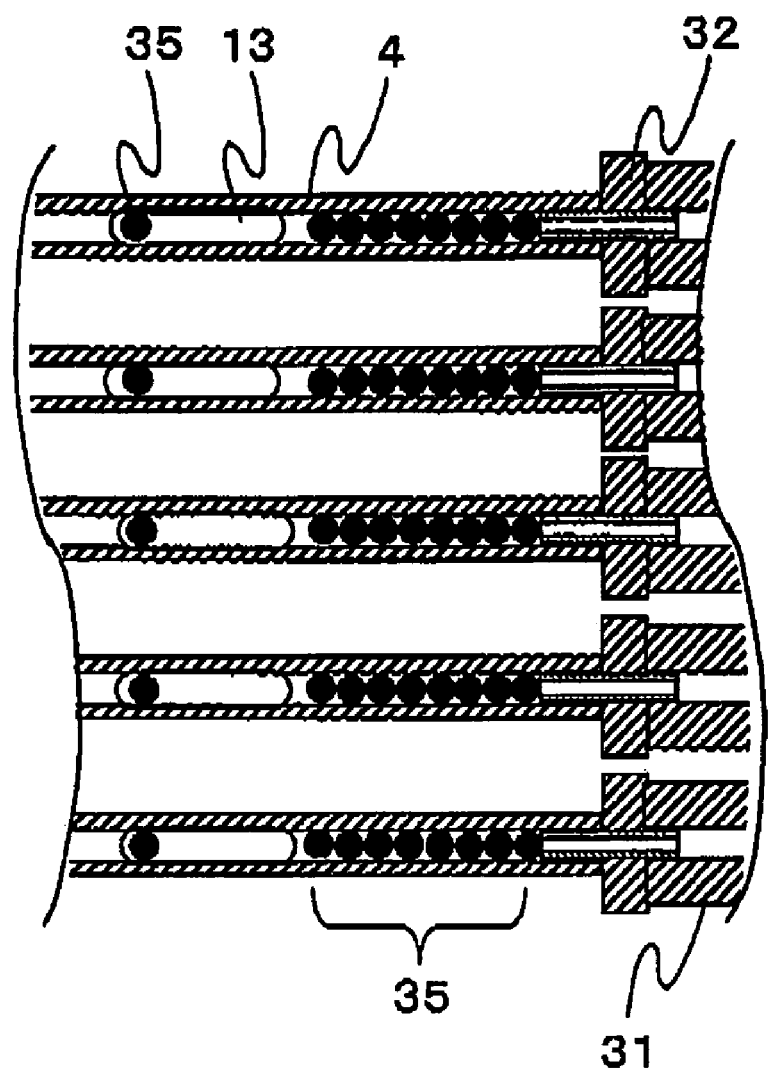
FIG. 11 is a schematic view showing a situation where the particles are arrayed in five second liquid transport pipes.

FIG. 11 is a schematic view showing a situation where the particles 35 are in process of being arrayed in the five second liquid transport pipes 4 arranged in the x-y plane. The ninth particles 35 are just about to be introduced while being enclosed in the liquid sections 13. As shown in FIG. 11, the parallel arrangement of the particle manipulating means shown in FIG. 9 makes it possible to fabricate five particle arrays at a time in the second liquid transport pipes 4, each particle array being formed of an array of nine types of the particles 35. Referring to the third embodiment, description is given using as an example the particle accommodating plate 20 having the accommodating units, the number of which is forty, that is, five by eight (5×8), for the sake of simplicity; however, the titer plate with 384 holes is actually used as the particle accommodating plate 20 to thereby prepare the particle capturing nozzles 25, the first liquid transport pipes 3, and the second liquid transport pipes 4, the numbers of which are each sixteen. This makes it possible to fabricate sixteen particle arrays at a time, each particle array being formed of an array of 24 types of the particles 35. Of course, the particle accommodating plates 20, the number of which is two or more, may be mounted on the second motor-driven actuator 23 in order that many, 25 or more, different types of particles are arrayed in each of the second liquid transport pipes 4.

FIG. 10 shows an illustrative instance where the first liquid transport pipes 3 and the second liquid transport pipes 4 are additionally disposed in units of plural pipes in n layers. A three-layer stacked structure in the direction of the z axis is shown in FIG. 10 for the sake of simplicity; however, more than three layers may be stacked one on top of another, provided that space permits. For example, the use of the titer plate with 384 holes as the particle accommodating plate 20 for the use of the sixteen particle capturing nozzles 25 enables a user to do a single setup for automatic fabrication of (16×n) particle arrays.

Fourth Embodiment

Figure 12:
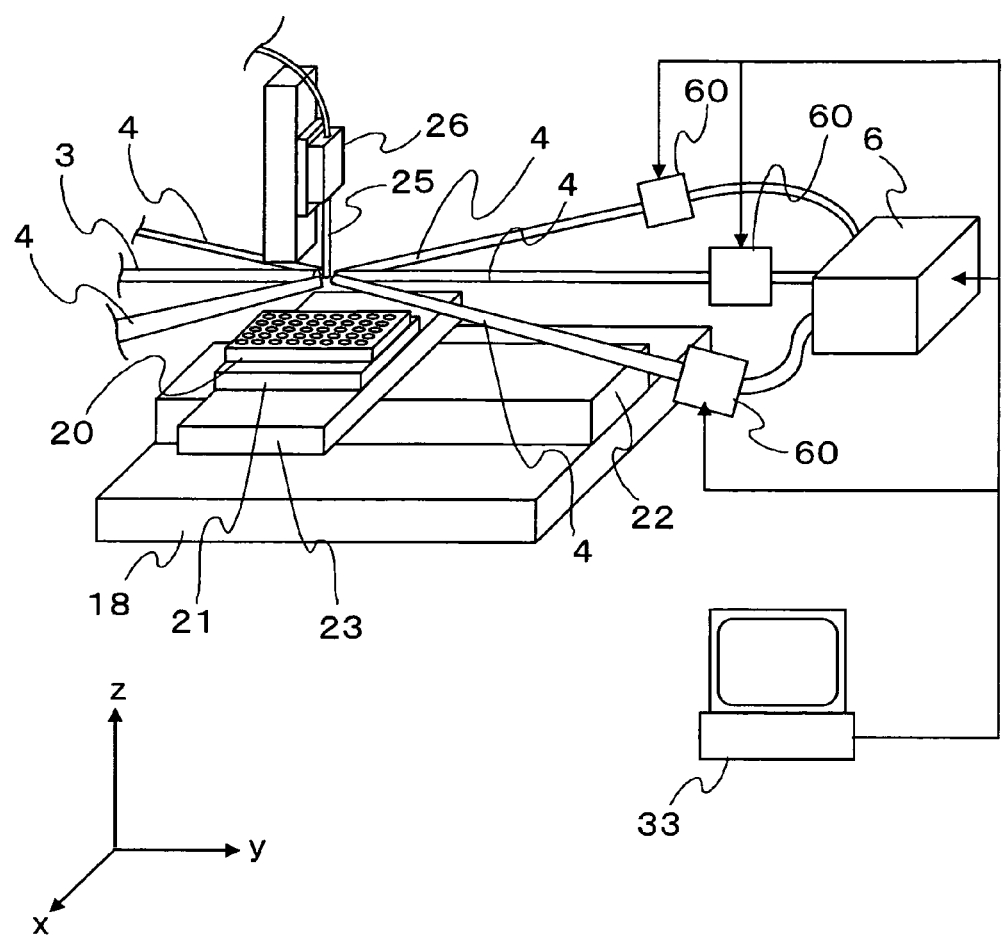
FIG. 12 is a schematic view showing an example of apparatus configuration of the present invention having a parallel arrangement of the second liquid transport pipes.
Figure 13:
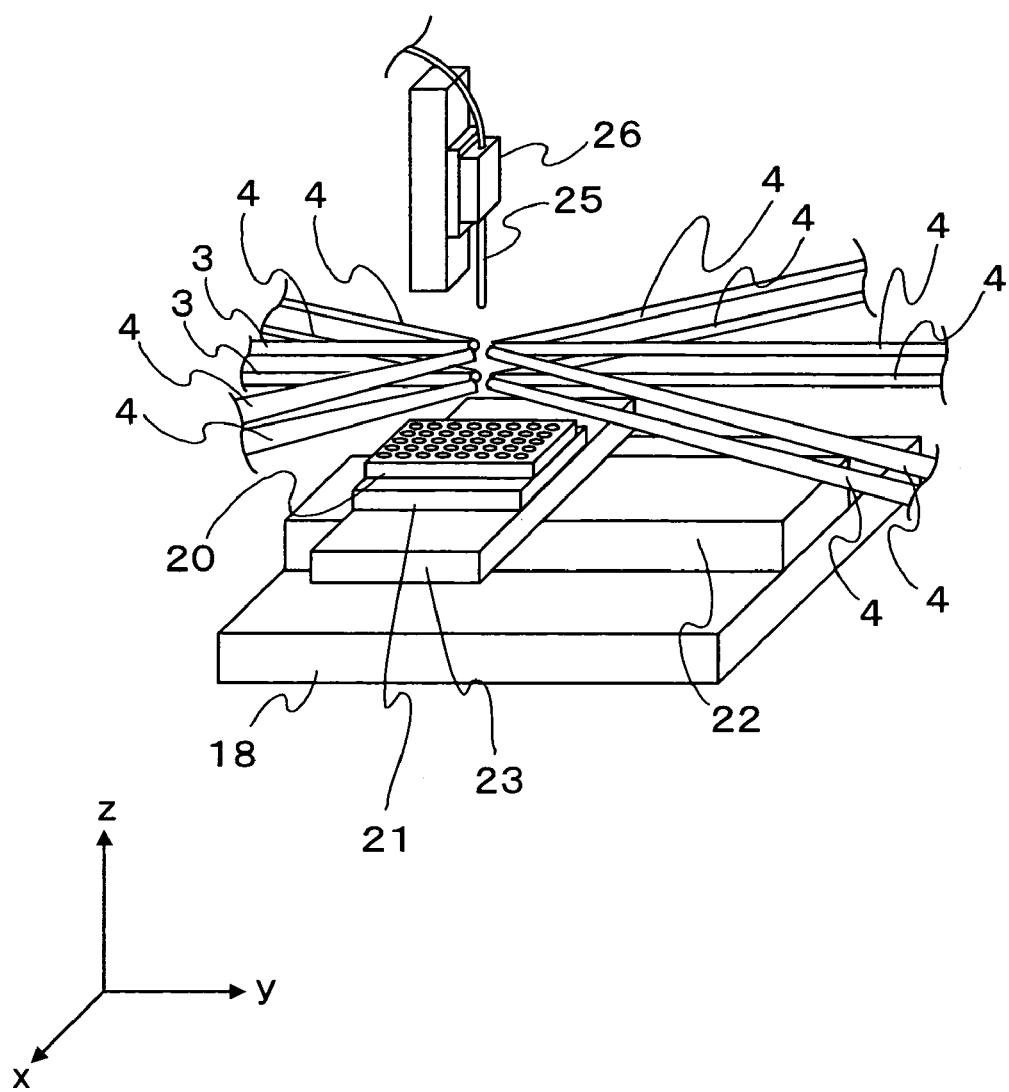
FIG. 13 is a schematic view showing an example of apparatus configuration of the present invention having a parallel arrangement of the second liquid transport pipes.

FIGS. 12 and 13 show two examples of apparatus configuration of the particle manipulating apparatus described with reference to FIG. 6 and FIGS. 7(A) to 7(G), having a parallel arrangement of the second liquid transport pipes 4 for use as the particle arrays, for one particle capturing nozzle 25 and one first liquid transport pipe 3.

To simplify description of FIG. 12, FIGS. 14(A) to 14(D) show cross-sectional views taken on the same x-y plane in which the first liquid transport pipe 3, and the second liquid transport pipes 4, the number of which is three, are arranged 90° apart. Up to 24 transport pipes can be installed in steps of 15°, depending on the outside diameters of the first liquid transport pipe 3 and the second liquid transport pipe 4, and further, the length of the air gap 11. Of course, the transport pipes are not limited to being arranged at regular equal intervals.

Figure 14A:
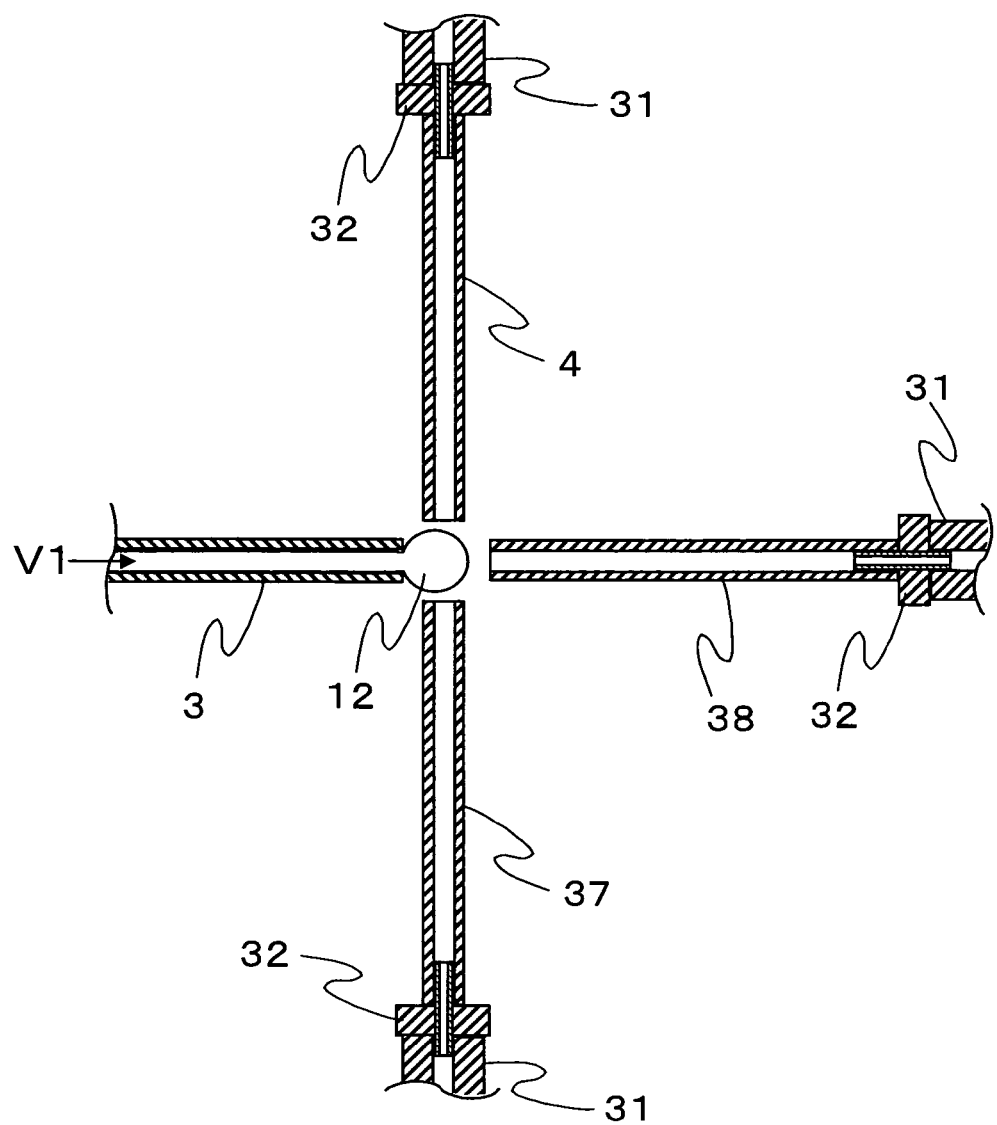
FIG. 14(A) is a schematic view showing an embodiment in which a first liquid transport pipe and the second liquid transport pipes are radially arranged.
Figure 14B:
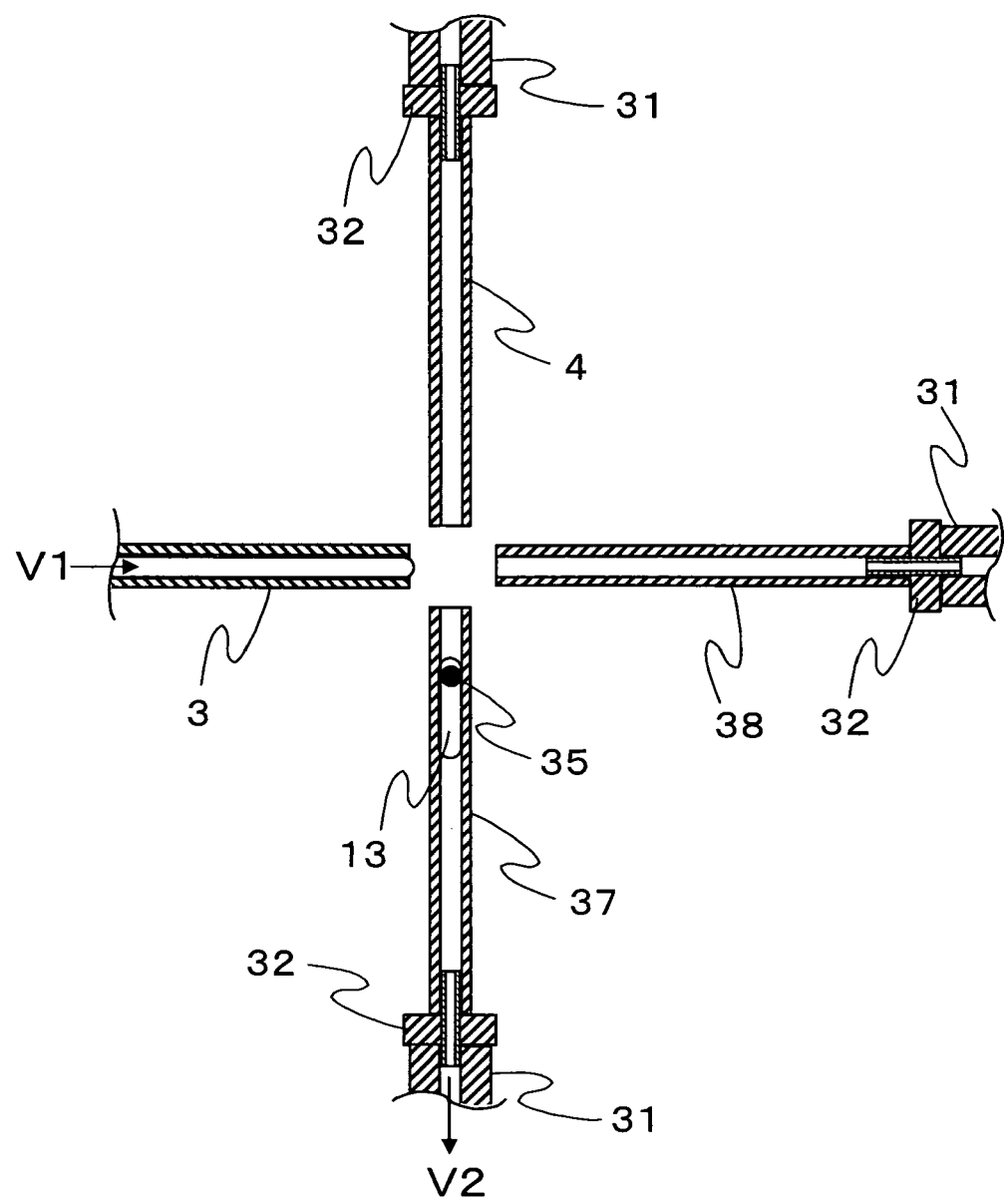
FIG. 14(B) is a schematic view showing a situation where the particle enclosed in the liquid droplet is introduced into a second liquid transport pipe.
Figure 14C:
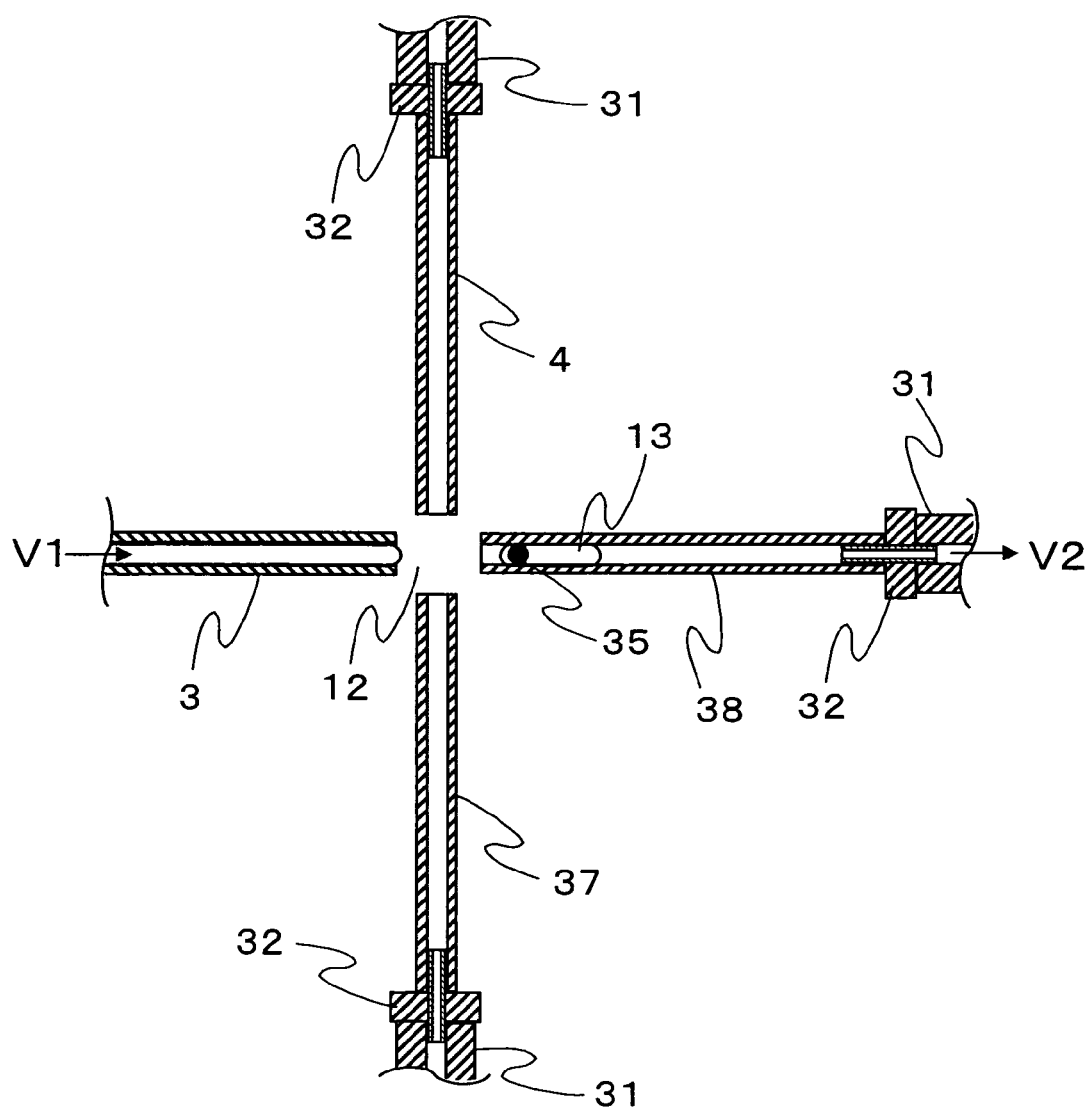
FIG. 14(C) is a schematic view showing a situation where the particle enclosed in the liquid droplet is introduced into a second liquid transport pipe.
Figure 14D:
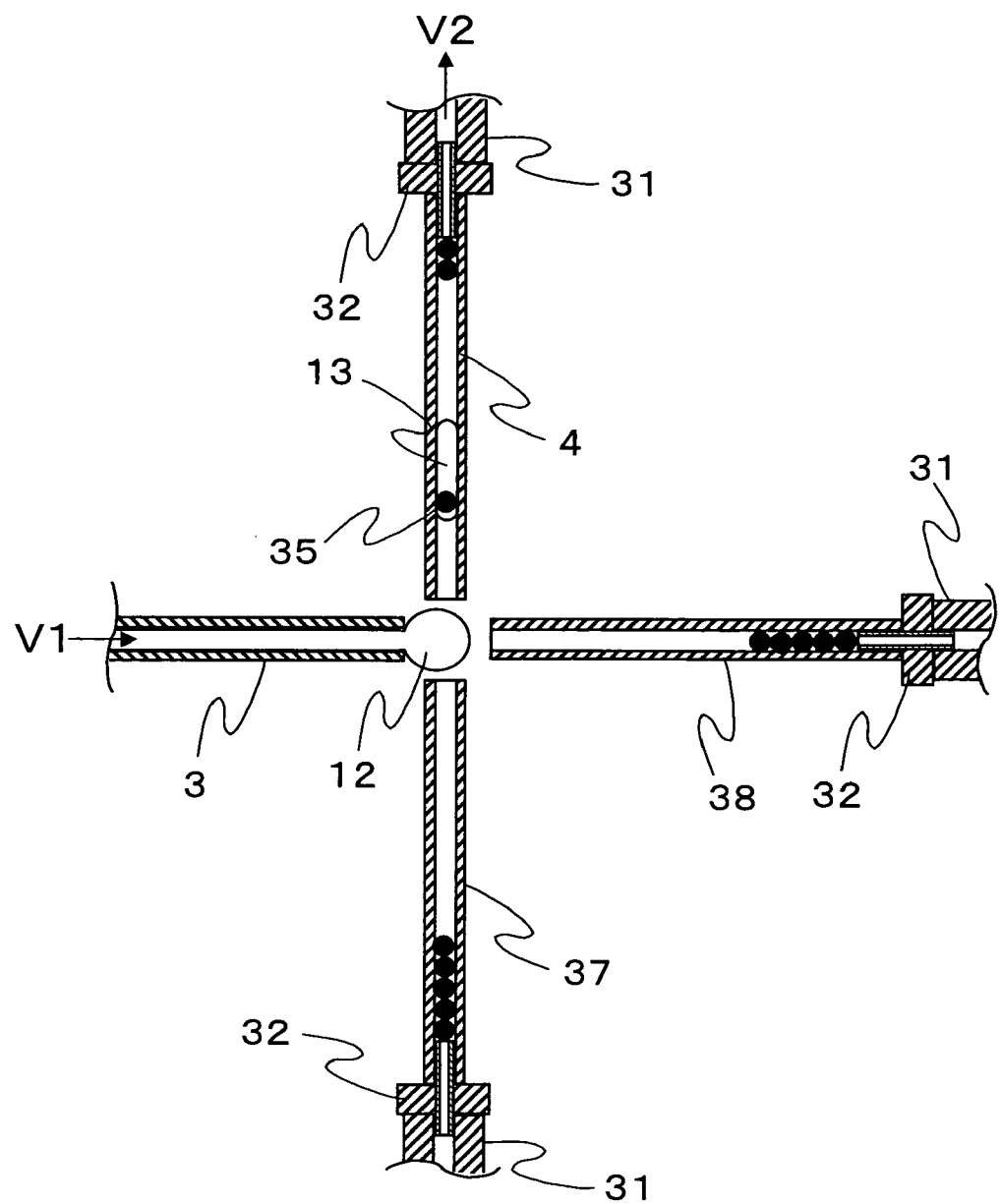
FIG. 14(D) is a schematic view showing a situation where particle arrays are fabricated in plural second liquid transport pipes.

FIG. 14(B) shows a situation where the particle 35 enclosed in the liquid droplet is introduced into a second liquid transport pipe 37. On the other hand, FIG. 14(C) shows a situation where the particle 35 enclosed in the liquid droplet is introduced into a second liquid transport pipe 38. Particle dispensing control as shown in FIGS. 14(B) and 14(C) can be changed under control of the suction pump 6 linked to the second liquid transport pipes 4. These controls are performed by the controller (the computer) 33, based on special-purpose software having a timing control function. Specifically, when the second liquid transport pipe 37 alone is under negative pressure as shown in FIG. 14(B) or the second liquid transport pipe 38 alone is under negative pressure as shown in FIG. 14(C), valves 60 shown in FIG. 12 are independently controlled to form closed circuits, thereby keeping the other second liquid transport pipes 4 from being subjected to a negative pressure by the suction pump 6. FIG. 14(D) is a schematic view showing a situation where the particle arrays are fabricated counterclockwise sequentially, starting at the second liquid transport pipe 37.

The apparatus configuration described with reference to FIG. 12 and FIGS. 14(A) to 14(D) is characterized by the feature of being able to array all particles 35 in the accommodating units 19 of the particle accommodating plate 20 in the second liquid transport pipes 4. For example, the titer plate with 384 holes is used as the particle accommodating plate 20, and the first liquid transport pipe 3, and the second liquid transport pipes 4, the number of which is 23, are prepared. This makes it possible to fabricate 23 particle arrays at a time, each particle array being formed of an array of 384 types of the particles 35. Of course, the particle accommodating plates 20, the number of which is two or more, may be mounted on the second motor-driven actuator 23 in order that 385 or more different types of particles are arrayed.

FIG. 13 shows an illustrative instance where the first liquid transport pipes 3 and the second liquid transport pipes 4 are additionally disposed in units of plural pipes in n layers in the direction of the z axis. A two-layer stacked structure in the direction of the z axis is shown in FIG. 13 for the sake of simplicity; however, still more than two layers may be stacked one on top of another, provided that space permits. This enables a user to do a single setup for automatic fabrication of (23×n) particle arrays.

Fifth Embodiment

Referring to the fifth embodiment, there are illustratively given the fabrication of the particle array intended for DNA detection, using the apparatus shown in FIG. 9, and a reaction test and a fluorescence detection test using the fabricated particle array.

Figure 15:
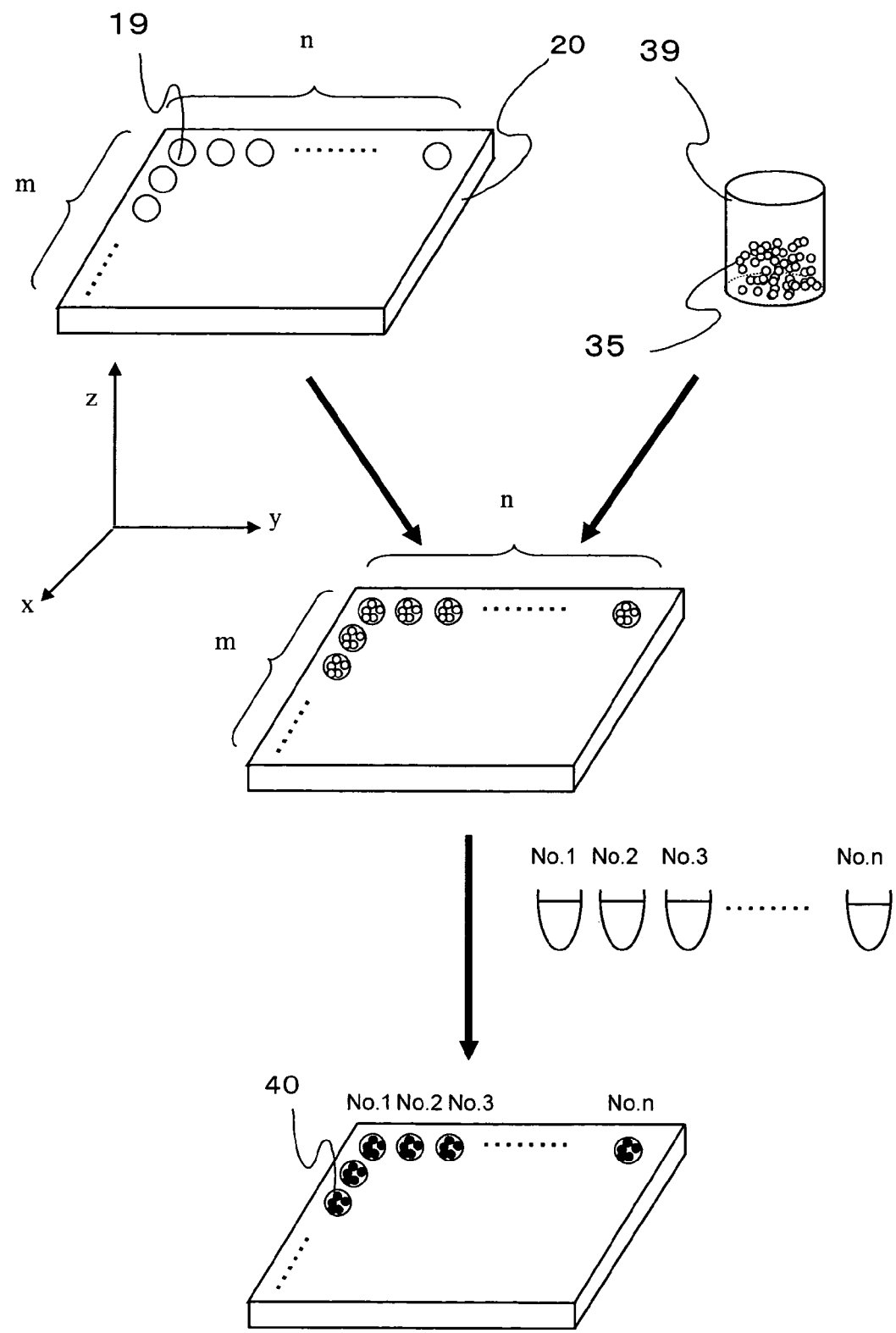
FIG. 15 is an explanatory view of assistance in explaining a particle preparation method and an example of the configuration of a particle accommodating plate.

Firstly, description will be given with reference to FIG. 15 with regard to a preparation method for particles having biomolecules immobilized on the surfaces. The particle accommodating plate 20 having the (m×n) accommodating units 19, a particle group, and plural types of biomolecular probes, such as DNA, RNA or protein, that modify the particles 35 are prepared. The accommodating units 19 of the particle accommodating plate 20 prepared are disposed at equally spaced intervals of first center-to-center spacing in the direction of the x axis, and are disposed at equally spaced intervals of second center-to-center spacing in the direction of the y axis perpendicular to the direction of the x axis. The accommodating units 19 each have the form of a cylindrical or conical hole having a circular opening at the top, having the central axis parallel to the direction of the z axis, and having the bottom. A commercially available micro titer plate with 96 holes or with 384 holes can be used as the particle accommodating plate 20 having the plural accommodating units 19 as mentioned above. As for the size of the particle 35, it is preferable that a spherical particle of 10 μm or more in diameter be used if the particle capturing nozzle 25 is made of glass.

The particles 35 prepared in units of a few milligrams are dispensed from a particle container 39 to each of the accommodating units 19 of the particle accommodating plate 20 by use of a medicine spoon, different types of probes are introduced into a column of the accommodating units 19 as a unit or into each of the accommodating units 19, and the probes are immobilized on the surfaces of all particles. This enables preparing the particle accommodating plate 20 holding plural types of probe-immobilized particles 40 each brought into correspondence with the type of probe according to the position of the accommodating unit 19.

In the fifth embodiment, n types of biomolecular probes are prepared, the biomolecular probes having "No. 1" assigned thereto are introduced into the m accommodating units belonging to the first column; the biomolecular probes having "No. 2" assigned thereto, into the m accommodating units belonging to the second column; . . . ; and the biomolecular probes having "No. n" assigned thereto, into the m accommodating units belonging to the nth column, and the probes are immobilized on the particles 35 accommodated in each of the accommodating units 19. If the probes immobilized on the particles 35 are chemically relatively stable biomolecules such as DNA, the particle accommodating plate 20 previously fabricated can be preserved in a desiccator or a refrigerator, and thus, the fabricated plates 20 can be kept in stock. The particle accommodating plate 20 having the accommodating units 19 each having a solution such as pure water introduced therein is mounted on the plate mounting jig 21 of the particle array apparatus shown in FIG. 9, and the particle arrays are fabricated by the process of operation described with reference to FIGS. 7(A) to 7(G).

Figure 16:
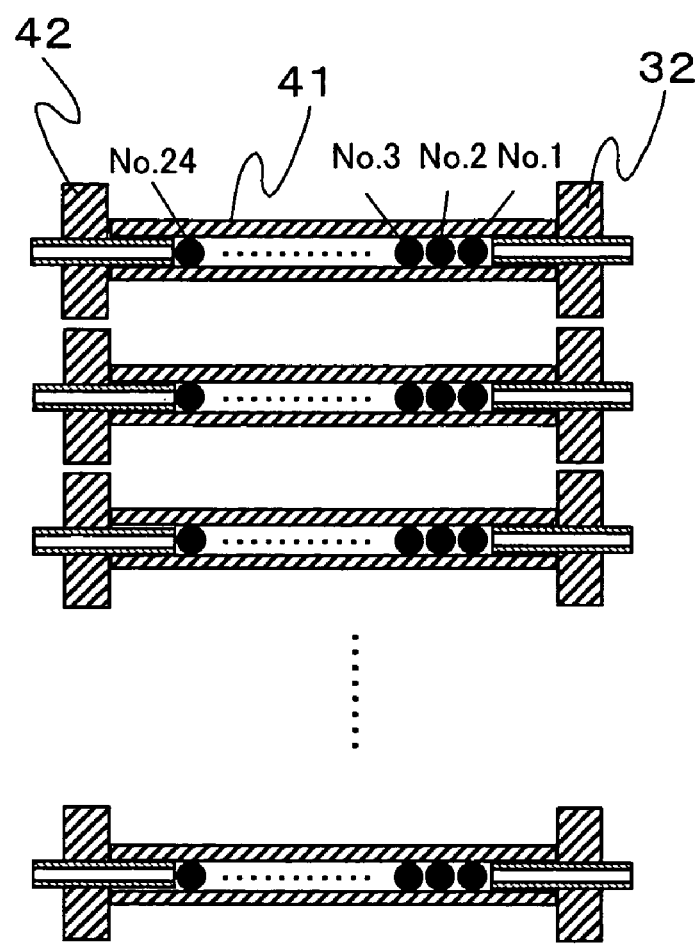
FIG. 16 is a schematic cross-sectional view of m particle array containers in which the particles are arrayed.

FIG. 16 is a cross-sectional view showing in schematic form an example of m particle array containers 41 obtained by use of the particle accommodating plate 20 having the (m×n) accommodating units 19 according to the fifth embodiment. The particle array container 41 is the second liquid transport pipe 4. At this stage, second sockets 42 each having a hollow capillary whose outside diameter coincides with the inside diameter of the particle array container 41 are inserted into the open end parts so as to prevent the particles 35 introduced into the particle array containers 41 from spilling out of the containers and also to keep the particles 35 in orderly array. Thereby, the first sockets 32 and the second sockets 42 can have the particle arrays sandwiched therebetween and thus prevent movement of the particles.

Description will now be given with reference to FIGS. 17(A) and 17(B) with regard to an example of the use of a DNA probe array using particles, for hybridization.

First, the particle manipulating apparatus shown in FIG. 9 using the micro titer plate with 384 holes as the particle accommodating plate 20 was used to array 24 types of DNA-immobilized particles in sequence and thereby fabricate the particle arrays in the sixteen particle array containers 41 at a time.

Figure 17A:
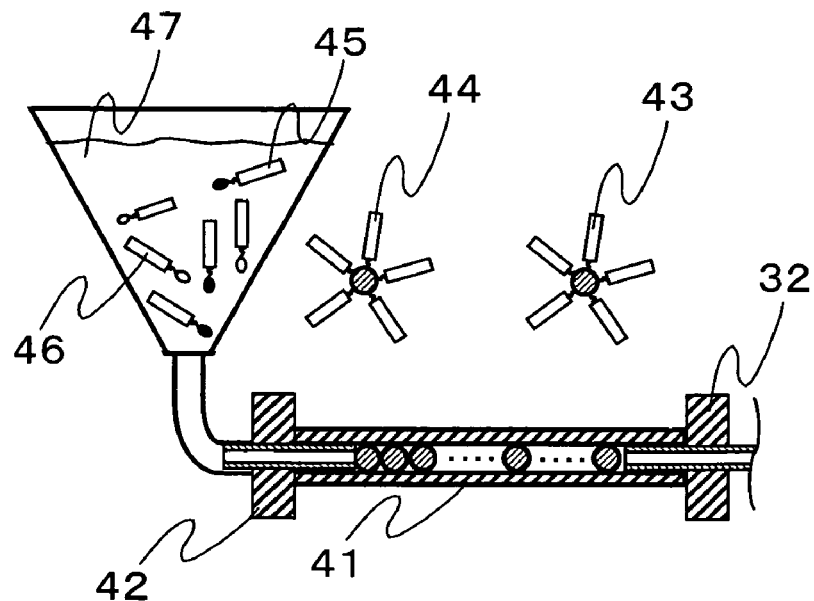
FIG. 17(A) is a schematic view showing an embodiment of a hybridization test using the particle array.
Figure 17B:
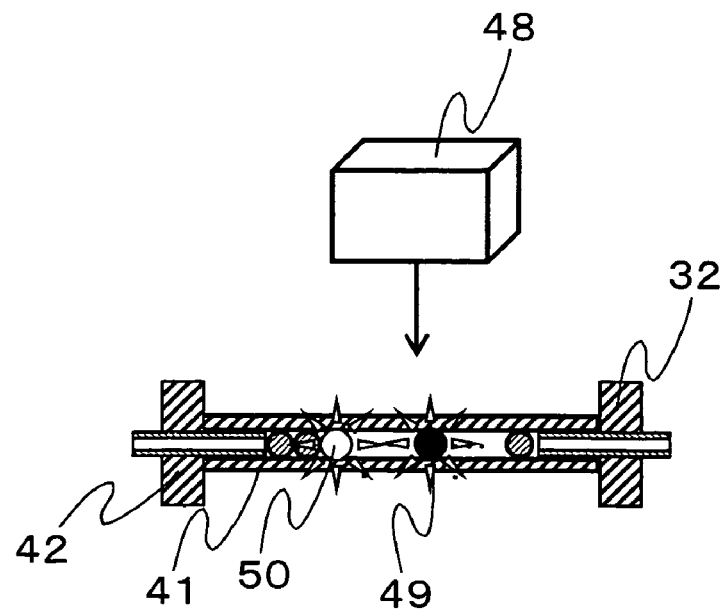
FIG. 17(B) is a schematic view showing a situation where fluorescence detection takes place after hybridization.

Referring to FIGS. 17(A) and 17(B), a sample containing single stranded target DNA 45 having a Cy3-labeled sequence 3 complementary to a sequence 1 and TexasRed-labeled single stranded target DNA 46 having a sequence 4 complementary to a sequence 2 was fed through the particle array container 41 having a particle having immobilized thereon a single stranded DNA probe 43 having the sequence 1 and a particle having immobilized thereon a single stranded DNA probe 44 having the sequence 2, of 24 types of probe DNA of synthetic oligonucleotide of 18 bases modified with 24 types of 5'-thiol groups having different base sequences, and verification was conducted as to whether the target DNA is bonded to the probe DNA as intended.

```
Sequence 1:    5'-thiol-ATCTGACT . . . GCTCCTC-3'

Sequence 2:    5'-thiol-CTACCTGC . . . CTGGACG-3'

Sequence 3:    5'-Cy3-GAGGAGCC . . . GTCAGAT-3'

Sequence 4:    5'-TexasRed-CGTCCAGG . . . CAGGTAG-3'
```

As shown in FIG. 17(A), a 20 mM phosphate buffer solution 47 (having a pH of 7.0) containing the single stranded target DNA 45 and the single stranded target DNA 46 each in a concentration of 1 μM was fed into and through the particle array container 41 having the DNA probe array fabricated therein, and hybridization reaction occurred at 45 degrees. A syringe pump was used for liquid feeding. After the reaction, residual target DNA that had not contribute to the hybridization reaction was cleaned in turn with the 20 mM phosphate buffer solution 47 (having a pH of 7.0) and pure water, and was dried. After that, the particles in the particle array container 41 were observed by a fluorescence microscope 48, using in turn a longpass filter for Cy3 and a longpass filter for TexasRed, centered at luminescence wavelengths of Cy3 and TexasRed, using a mercury lamp as a light source.

As a result, it has been observed that a predetermined particle of the arrayed particles emits Cy3 fluorescence 49, and further, another predetermined particle emits TexasRed fluorescence 50, as shown in FIG. 17(B). This suggests that the single stranded target DNA 45 was reliably hybridized with the single stranded DNA probe 43; and the single stranded target DNA 46, with the single stranded DNA probe 44, and it has been shown that this particle manipulating apparatus can fabricate the DNA probe array in the particle array container 41 in any given sequence without affecting the probe.

Sixth Embodiment

Analyzers for detecting the quantity of constituent contained in a sample such as blood or serum include a spectrometry technology that involves irradiating a reactant solution, which is a mixed solution of the sample and a reagent, with white light from a halogen lamp or the like; extracting a required wavelength component by a diffraction grating performing spectrometry on the light that has passed through the reactant solution; and calculating the absorbance of the mixed solution, thereby measuring a target constituent quantity, while recently there has been an increasing need to achieve a trace quantity for purposes of reagent cost reduction. Referring to the sixth embodiment, description will be given with regard to an instance where a trace liquid is used as a transport object.

Figure 18A:
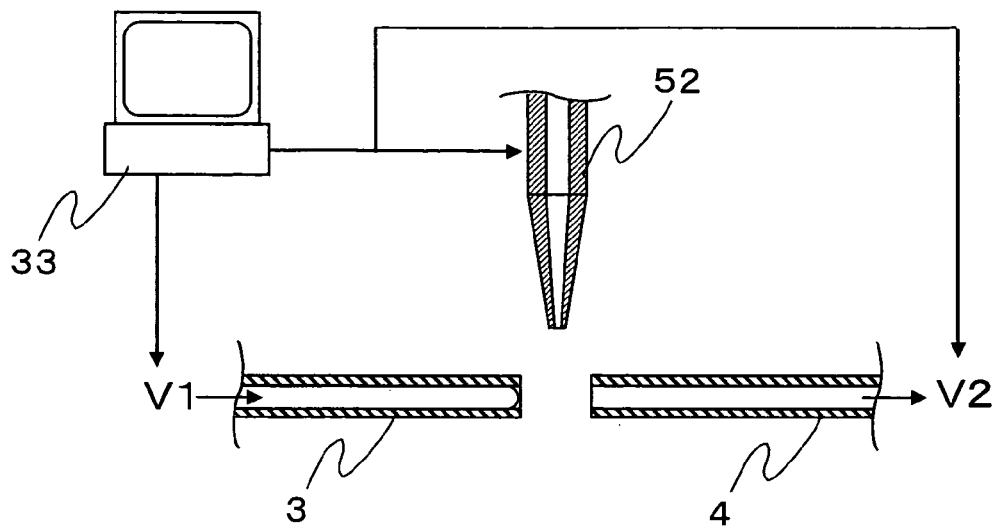
FIG. 18(A) is a schematic view showing a situation where oil flows through the first liquid transport pipe.
Figure 18B:
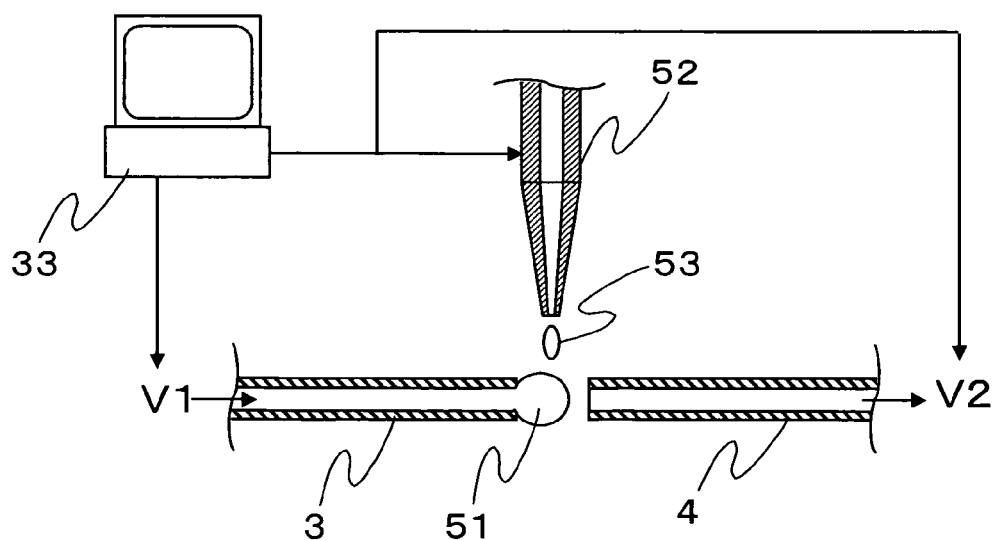
FIG. 18(B) is a schematic view showing the formation of an oil droplet.
Figure 18C:
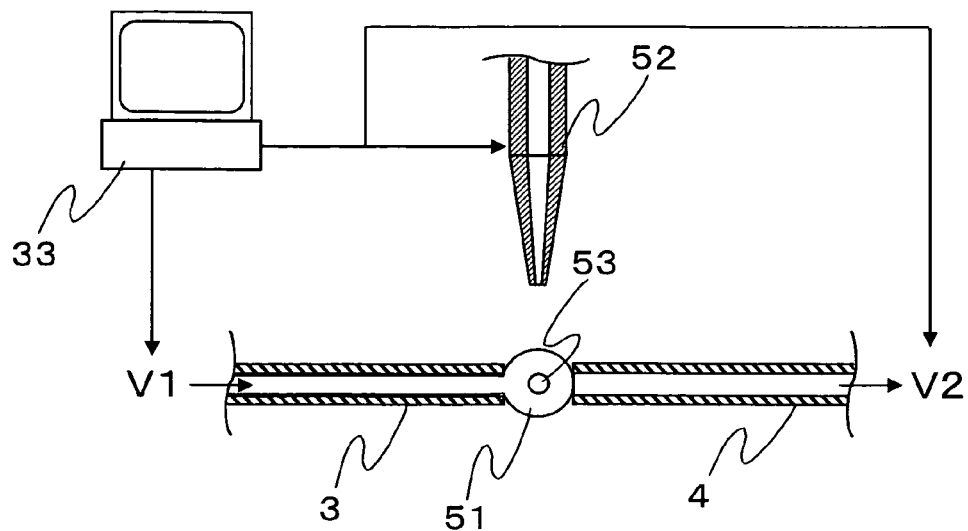
FIG. 18(C) is a schematic view showing a situation where a trace liquid ejected from a dispensing nozzle is enclosed in the oil droplet.
Figure 18D:
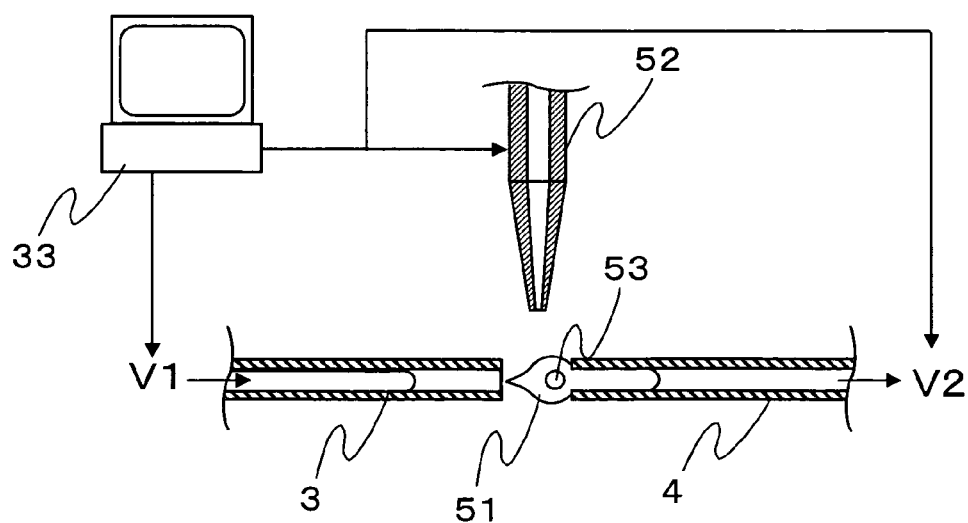
FIG. 18(D) is a schematic view showing the instant at which the oil droplet having the trace liquid enclosed therein moves into the second liquid transport pipe.
Figure 18E:
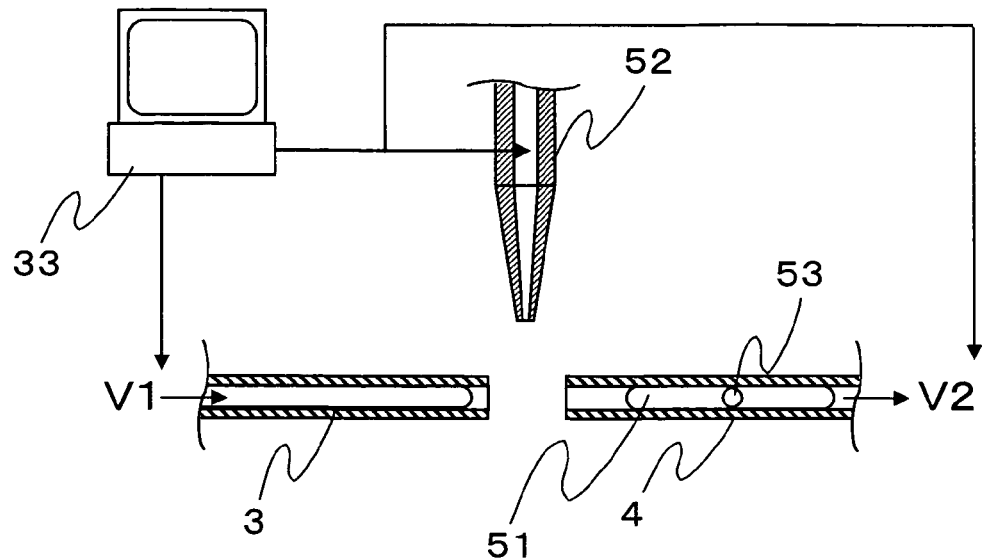
FIG. 18(E) is a schematic view showing a situation where the particle enclosed in the liquid section is transported.

FIGS. 18(A) to 18(E) are schematic views showing a situation where a trace liquid 53 is enclosed in an oil droplet 51 and is transported as enclosed therein. FIG. 18(A) shows an instant immediately before oil is just about to exit from the first liquid transport pipe 3 and form the oil droplet 51. FIG. 18(B) shows the instant at which the oil exits through the liquid outlet 9 of the first liquid transport pipe 3 and forms the oil droplet 51 in the air gap 11. FIG. 18(C) shows a situation where the trace liquid 53 ejected from a liquid dispensing nozzle 52 into the oil droplet 51 is enclosed in the oil droplet 51. As shown in FIGS. 18(D) and 18(E), the enclosed trace liquid 53 is transported, as held in the oil droplet 51, into the second liquid transport pipe 4.

The timing of ejection of the trace liquid 53 from the liquid dispensing nozzle 52 is synchronized to the formation of the oil droplet 51 by use of the controller (the computer) 33. A vision sensor or CCD camera or a line sensor can be used as a detecting means for providing synchronization. The ejection of the trace liquid 53 is effected by sending a signal to the controller 33 while making a direct observation of the oil droplet 51. Alternatively, the ejection of the trace liquid 53 may be effected by monitoring an interval between oil sections flowing through the second liquid transport pipe 4; determining regularity in the interval; sending data on the regularity to the controller 33; and providing appropriate timing for the ejection of the trace liquid 53.

Figure 19:
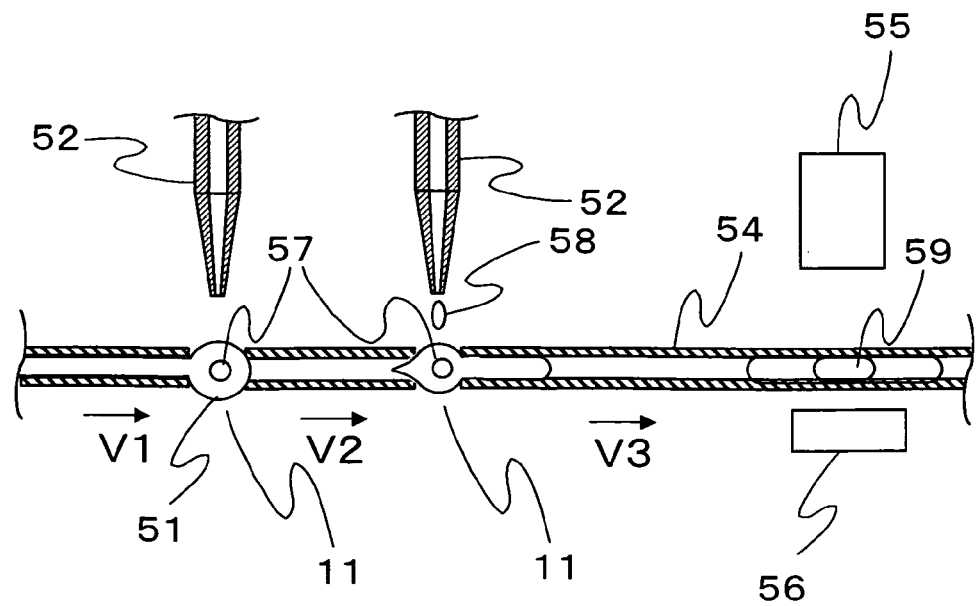
FIG. 19 is a schematic view showing an example of a trace liquid manipulating apparatus of the present invention.

FIG. 19 is a schematic view showing an example of a trace liquid manipulating apparatus of the present invention. FIG. 19 shows an instance where the air gaps 11 are interposed in two places, and thus, in the air gaps 11, a sample solution droplet 57 and a reagent solution droplet 58 can be fed into the oil droplet 51 transported from the liquid container 1. The first liquid transport pipe 3, the second liquid transport pipe 4, and a detection cell liquid transport pipe 54 are equipped with the first liquid feed pump 2, the second liquid feed pump 15, and a third liquid feed pump, respectively, so as to enable transporting the liquid section while holding the liquid section. Flow velocity conditions for the pipes are V1<V2≦V3, and a peristaltic pump will conveniently be used for velocity control.

A detection region that forms a portion of the detection cell liquid transport pipe is provided with a light source 55 and a detector 56, which are used to measure the absorbance of a mixed solution 59 of the sample solution droplet 57 and the reagent solution droplet 58 mixed in the oil droplet 51. Here, a spectroscope and a condenser lens are omitted from FIG. 19 for the sake of simplicity. The reason for the sixth embodiment using the oil droplet 51 is to prevent contamination in the transport pipes and crossover on the occasion of continuous measurement. The use of the oil enables preventing the sample and the reagent from being adsorbed on the walls of the transport pipes.

The invention claimed is:
1. A liquid droplet formation and transport apparatus comprising:
a first liquid transport pipe;
a first liquid feed means for supplying a liquid to the first liquid transport pipe and feeding the liquid through the first liquid transport pipe at a velocity V1;

a second liquid transport pipe whose liquid inlet is disposed at a liquid outlet of the first liquid transport pipe with an air gap in between; and a second liquid feed means for sucking the liquid through the liquid inlet of the second liquid transport pipe and conveying the liquid through the second liquid transport pipe at a velocity V2, wherein V1<V2, whereby the liquid exits through the liquid outlet of the first liquid transport pipe and forms a liquid droplet in the air gap, the liquid droplet is sucked through the liquid inlet of the second liquid transport pipe, and the liquid droplet, along with a respective intermittent fluid of air in front and behind the liquid droplet, are conveyed through the second liquid transport pipe.

2. The liquid droplet formation and transport apparatus according to claim 1, characterized in that the liquid outlet of the first liquid transport pipe and the liquid inlet of the second liquid transport pipe are coaxially oppositely disposed.

3. The liquid droplet formation and transport apparatus according to claim 1, characterized in that a plurality of first liquid transport pipes and a plurality of second liquid transport pipes are arranged in the same plane, and the first liquid transport pipes are in a one-to-one correspondence with the second liquid transport pipes.

4. The liquid droplet formation and transport apparatus according to claim 3, characterized in that the first liquid transport pipes and the second liquid transport pipes are disposed in a plurality of layers in a direction perpendicular to the plane.

5. The liquid droplet formation and transport apparatus according to claim 1, characterized in that the air gap is equal to or less than 2 mm.

6. The liquid droplet formation and transport apparatus according to claim 1, characterized in that one first liquid transport pipe and a plurality of second liquid transport pipes are radially arranged so that one liquid outlet and a plurality of liquid inlets are located equidistantly from the center of the air gap, and characterized by comprising a means for selecting one of the plurality of second liquid transport pipes to suck in the liquid droplet formed in the air gap after exiting from the first liquid transport pipe.

7. The liquid droplet formation and transport apparatus according to claim 1, characterized in that the liquid supplied to the first liquid transport pipe is any one of water, a buffer solution, a biomolecular sample, and oil.

8. The liquid droplet formation and transport apparatus according to claim 1, characterized by comprising:

a means for introducing air into the first liquid transport pipe and thereby partitioning the incoming liquid with the air;

a means for controlling the timing of introduction of the air into the first liquid transport pipe; and a trace dispensing means for ejecting a predetermined number of liquid samples, each having a predetermined volume, fed intermittently to the second liquid transport pipe, at an open end opposite to the liquid inlet of the second liquid transport pipe.

9. The liquid droplet formation and transport apparatus according to claim 1, characterized in that the volume of the liquid droplet is controlled by controlling the length of the air gap.

10. A particle manipulating apparatus comprising:

a first liquid transport pipe;

a first liquid feed means for supplying a liquid to the first liquid transport pipe and feeding the liquid through the first liquid transport pipe at a velocity V1;

a second liquid transport pipe whose liquid inlet is disposed at a liquid outlet of the first liquid transport pipe with an air gap in between;

a second liquid feed means for sucking the liquid through the liquid inlet of the second liquid transport pipe and conveying the liquid through the second liquid transport pipe at a velocity V2, wherein V1<V2;

a particle accommodating unit that accommodates a particle;

a particle capturing nozzle having a tip, said particle capturing nozzle capable of moving while capturing, at the tip, a particle accommodated in the particle accommodating unit;

a pressure control means for controlling a pressure in the particle capturing nozzle; and a particle capturing nozzle driving means for effecting movement of the particle capturing nozzle between the particle accommodating unit and the air gap, whereby the liquid exits through the liquid outlet of the first liquid transport pipe and forms a liquid droplet in the air gap, the liquid droplet is sucked through the liquid inlet of the second liquid transport pipe, and the liquid droplet, along with a respective intermittent fluid of air in front and behind the liquid droplet, are conveyed through the second liquid transport pipe, and one particle sucked and captured from the particle accommodating unit as the tip of the particle capturing nozzle is moved via the particle capturing nozzle driving means, to the position of the liquid droplet formed in the air gap, by the first liquid transport pipe, and the particle is released from the particle capturing nozzle under pressure control of the pressure control means, into and enclosed in the liquid droplet, and is transported into the second liquid transport pipe.

11. The particle manipulating apparatus according to claim 10, further comprising a biological probe immobilized on the particle.

12. The particle manipulating apparatus according to claim 10, characterized in that the number of particle capturing nozzles is equal to or smaller than the number of first liquid transport pipes.

13. The particle manipulating apparatus according to claim 10, characterized by comprising a particle accommodating plate having a plurality of particle accommodating units having biological-probe-immobilized particles accommodated therein, the particle manipulating apparatus characterized in that the biological-probe-immobilized particles accommodated in the plurality of particle accommodating units are transported in predefined sequence into the second liquid transport pipe, whereby a probe array is fabricated in the second liquid transport pipe or in a particle array container connected to the second liquid transport pipe.

14. The particle manipulating apparatus according to claim 13, wherein that the inside diameter of at least one of (a) the second liquid transport pipe and (b) the particle array container is:

(i) larger than the diameter of the biological-probe-immobilized particle, and (ii) is smaller than twice the diameter of the particle.

15. The particle manipulating apparatus according to claim 13, characterized by comprising a stage that moves while holding the particle accommodating plate, the particle manipulating apparatus characterized in that the particle capturing nozzle driving means effects upward and downward movements of the particle capturing nozzle, and the stage effects horizontal movement of the particle accommodating plate.

16. The particle manipulating apparatus according to claim 10, characterized in that one first liquid transport pipe and a plurality of second liquid transport pipes are radially arranged so that one liquid outlet and a plurality of liquid inlets are located equidistantly from the center of the air gap, and characterized by comprising a means for selecting one of the plurality of the second liquid transport pipes to suck in the liquid droplet formed in the air gap after exiting from the first liquid transport pipe.

17. A trace liquid transport apparatus comprising:
a first liquid transport pipe;
a first liquid feed means for supplying a liquid to the first liquid transport pipe and feeding the liquid through the first liquid transport pipe at a velocity V1;
a second liquid transport pipe whose liquid inlet is disposed at a liquid outlet of the first liquid transport pipe with an air gap in between;
a second liquid feed means for sucking the liquid through the liquid inlet of the second liquid transport pipe and conveying the liquid through the second liquid transport pipe at a velocity V2, wherein V1<V2; and
a trace dispensing means for adding a liquid sample,
whereby the liquid exits through the liquid outlet of the first liquid transport pipe and forms a liquid droplet in the air gap, the liquid droplet is sucked through the liquid inlet of the second liquid transport pipe, and the liquid droplet, along with a respective intermittent fluid of air in front and behind the liquid droplet, are conveyed through the second liquid transport pipe, and the trace dispensing means adds the liquid sample to the liquid droplet formed in the air gap.

18. The trace liquid transport apparatus according to claim 17, characterized in that the liquid supplied to the first liquid transport pipe is immiscible with the liquid sample.

19. A liquid droplet formation and transport method, said method comprising the steps of:
feeding a liquid to a first liquid transport pipe and feeding the liquid through the first liquid transport pipe at a velocity V1;
forming a liquid droplet in a liquid outlet at an open end of the first liquid transport pipe; and
sucking the liquid droplet through a liquid inlet at an open end of a second liquid transport pipe and feeding the liquid through the second liquid transport pipe at a velocity V2,
wherein the liquid flowing through the first liquid transport pipe and a liquid feed velocity V2 of the liquid flowing through the second liquid transport pipe is V1<V2, and
whereby the liquid droplet expands to the liquid inlet at the open end of the second liquid transport pipe and is then transported into the second liquid transport pipe as a liquid droplet with a respective intermittent fluid of air in front and behind the liquid droplet.

20. The liquid droplet formation and transport method according to claim 19, characterized in that the volume of the liquid droplet is controlled by adjusting the length of an air gap between the liquid outlet at the open end of the first liquid transport pipe and the liquid inlet at the open end of the second liquid transport pipe.

\* \* \* \* \*